US012782360B2

(12) United States Patent
Theuser et al.

(10) Patent No.: US 12,782,360 B2
(45) Date of Patent: Nov. 3, 2026

(54) METHOD AND REAGENTS FOR ENHANCING THE CHEMILUMINESCENT SIGNAL

(71) Applicant: EUROIMMUN Medizinische Labordiagnostika AG, Luebeck (DE)

(72) Inventors: Matthias Theuser, Luebeck (DE); Lars Komorowski, Luebeck (DE); Antje Dammermann, Luebeck (DE); Kathrin Baumert, Luebeck (DE); Mareike Holste, Luebeck (DE); Marcel Hinkelammert, Luebeck (DE)

(73) Assignee: EUROIMMUN Medizinische Labordiagnostika AG, Luebeck (DE)

(*) Notice: Subject to any disclaimer, the term of this patent is extended or adjusted under 35 U.S.C. 154(b) by 429 days.

(21) Appl. No.: 18/292,325

(22) PCT Filed: Jul. 21, 2022

(86) PCT No.: PCT/EP2022/070522
§ 371 (c)(1),
(2) Date: Jan. 25, 2024

(87) PCT Pub. No.: WO2023/006581
PCT Pub. Date: Feb. 2, 2023

(65) Prior Publication Data

US 2024/0353412 A1 Oct. 24, 2024

(30) Foreign Application Priority Data

Jul. 29, 2021 (EP) .................................... 21188638

(51) Int. Cl.
*G01N 1/00* (2006.01)
*C09K 11/07* (2006.01)
*G01N 33/58* (2006.01)

(52) U.S. Cl.
CPC ............ *G01N 33/582* (2013.01); *C09K 11/07* (2013.01); *C09K 2211/1007* (2013.01); *C09K 2211/1018* (2013.01)

(58) Field of Classification Search
None
See application file for complete search history.

(56) References Cited

U.S. PATENT DOCUMENTS 4,927,769 A 5/1990 Chang et al.
7,186,568 B1 * 3/2007 Akhavan-Tafti ..... G01N 33/533 436/805

(Continued)

FOREIGN PATENT DOCUMENTS

JP 11-506924 A 6/1999

OTHER PUBLICATIONS

Arakawa et al., "Development of a highly sensitive chemiluminescent assay for hydrogen peroxide under neutral conditions using acridinium ester and its application to an enzyme immunoassay", Luminescence, The Journal of Biological and Chemical Luminescence, vol. 29, No. 4, published online Jul. 5, 2013, pp. 374-377.

(Continued)

*Primary Examiner* — Jyoti Mutreja
(74) *Attorney, Agent, or Firm* — Grüneberg Global IP, PLLC

(57) ABSTRACT

A method for enhancing the chemiluminescent signal of a chemiluminogenic compound in a chemiluminescent reaction mixture in a chemiluminescent reaction which has a step of oxidizing the chemiluminogenic compound in the presence of an effective amount of an enhancer can be performed. To obtain an enhanced chemiluminescent signal, a compound selected from the group of quaternary amine cationic substances of formula (I) for enhancing the chemiluminescent signal of an acridinium compound is used, (Continued)

preferably an acridinium ester or an acridinium sulfonamide. The signal is obtained in a chemiluminescent reaction, preferably in a chemiluminescent immunoassay, a related chemiluminescent composition and a related kit.

18 Claims, 8 Drawing Sheets

(56) References Cited

U.S. PATENT DOCUMENTS

| | | | |
|---|---|---|---|
| 2011/0136103 | A1 | 6/2011 | Adamczyk et al. |
| 2012/0001136 | A1 | 1/2012 | Qian et al. |

OTHER PUBLICATIONS

International Search Report received for PCT Application No. PCT/EP2022/070522, mailed on Oct. 26, 2022, 4 pages.
Natrajan et al., "A comparison of chemiluminescent acridinium dimethylphenyl ester labels with different conjugation sites", Organic & Biomolecular Chemistry, vol. 13, accepted Jan. 2, 2015, pp. 2622-2633.
Written Opinion received for PCT Application No. PCT/EP2022/070522, mailed on Oct. 26, 2022, 4 pages.

* cited by examiner

METHOD AND REAGENTS FOR ENHANCING THE CHEMILUMINESCENT SIGNAL

CROSS-REFERENCE TO RELATED APPLICATIONS

This application is a National Stage entry under § 371 of International Application No. PCT/EP2022/070522, filed on Jul. 21, 2022, and which claims the benefit of priority to European Patent Application No. 21188638.7, filed on Jul. 29, 2021. The content of each of these applications is hereby incorporated by reference in its entirety.

BACKGROUND OF THE INVENTION

Field of the Invention

The present invention relates to a method for enhancing the chemiluminescent signal of a chemiluminogenic compound in a chemiluminescent reaction mixture in a chemiluminescent reaction which comprises oxidizing the chemiluminogenic compound in the presence of an effective amount of an enhancer to obtain an enhanced chemiluminescent signal, use of a compound selected from the group consisting of quarternary amine cationic substances of formula (I) for enhancing the chemiluminescent signal of an acridinium compound, preferably an acridinium ester or an acridinium sulfonamide, in a chemiluminescent reaction, preferably in a chemiluminescent immunoassay, a related chemiluminescent composition and a related kit.

Description of Related Art

As a non-radioactive immunoassay technology, chemiluminescence immunoassays developed very quickly in the world after enzyme immunoassay (EIA), radioimmunoassay, and fluorescence immunoassay technologies. The chemiluminescent immunoassay is a technology which has high sensitivity, wide detection range, simple and fast operation, stable label, and low contamination, making it a desirable quantitative immunoassay method (Cinquanta et al., "Chemiluminescent immunoassay technology: what does it change in autoantibody detection?," Auto Immun Highlights, 8:9, 24 Jun. 2017).

Nowadays, the chemiluminescence immunoassay is often preferred over traditional detection methods such as radioimmunoassay for the quantification of various biological substances such as small molecules, nucleic acids, hormones, antibodies etc. It is characterized by the generation of light by chemiluminogenic substrates due to an external stimulus by chemical or enzymatic trigger substances. Prominent examples of chemiluminogenic substrates are luminol, 1,2-dioxetane aryl phosphates, the Tris-(bipyridyl) ruthenium (II) complex or acridinium-based probes. Typically, the chemiluminescence reaction can be divided into flash-type and glow-type chemiluminescence depending on the nature of chemiluminogenic substrate, the applied trigger substances and the resultant type of light output. As described in Tannous et al. (Tannous et al., "Combined flash and glow-type chemiluminescent reactions for high-throughput genotyping of biallelic polymorphisms," Analytical Biochemistry, Volume 320, Issue 2, Pages 266-272, 15 Sep. 2003) the flash-type reaction results in a bright chemiluminescence signal in the range of seconds to minutes while the light output in glow-type reactions is not as bright but it can persist up to several hours. Depending on the method of choice, flash-type and glow-type immunoassays can be designed accordingly.

Flash-type acridinium-based probes are often used in chemiluminescence immunoassays for fast and ultra-sensitive signal generation if a high-throughput of samples is required. Prominent examples are 10-Methyl-2,6-dimethyl-acridinium-NHS ester (Me-DMAE-NHS), N-Sulfopropyl-dimethyl-acridinium-N-hydroxysuccinimide ester (NSP-DMAE-NHS), N-Sulfopropyl-acridinium-sulfonamide-N-hydroxysuccinimide ester (NSP-SA-NHS) and 10-Methyl-2,6-dimethyl-acridinium-(polyethylene oxide) 4-N-hydroxysuccinimide ester (MeAE-PEO4-NHS) and these molecules and variants thereof are, for example, described in EP 1273917 B1, EP 1539702 B1 and others. All of these molecules generate light upon the external stimuli by alkaline hydrogen peroxide. Typically, the latter reagents are added stepwise in trigger solutions A and B. Hydrogen peroxide is commonly part of trigger A in combination with an acid such as nitric acid. Sodium hydroxide is injected thereafter in trigger B.

For optimal signal generation trigger B additionally is supposed to require a detergent molecule which might form a micellular structure in aqueous solution. Chang and Miller describe in U.S. Pat. No. 4,927,769 that cationic detergents based on quarternary amines are especially favorable. Although non-ionic or anionic detergents are also possible, the positive charge in the head group of the cationic detergent is supposed to bring the mostly hydrophobic acridinium-based probe and the negatively charged hydrogen peroxide anion into spatial proximity at the micellular interface and thus, foster chemiluminescence signal output as also described in Natrajan et al. (Natrajan et al., "Effect of surfactants on the chemiluminescence of acridinium dimethylphenyl ester labels and their conjugates," Org. Biomol. Chem., 9, pp. 5092-5103, 13 April 2011). A prominent example of such a cationic detergent included in U.S. Pat. No. 4,927,769 is Cetyltrimethylammonium chloride (CTAC).

Nevertheless, additional improvements in the chemiluminescence immunoassay technology are required to allow for quantification of analytes with ultra-low concentration and to facilitate discrimination between signal and noise in general. These improvements most likely necessitate the enhancement of the chemiluminescence by optimized enhancer substances.

SUMMARY OF THE INVENTION

The problem underlying the present invention is to provide a method and related reagents and uses in the chemiluminescence immunoassay technology that can be used for improved quantification of analytes, especially with ultra-low concentration, and that can be used to better facilitate discrimination between signal and noise in general.

Another problem underlying the present invention is to provide substances that are able to enhance the chemiluminescent signal of a chemiluminogenic compound, preferably an acridinium compound as e.g. an acridinium ester or an acridinium sulfonamide, in a chemiluminescence immunoassay.

In a $1^{st}$ aspect, the problem underlying the present invention is solved by a method for enhancing the chemiluminescent signal of a chemiluminogenic compound in a chemiluminescent reaction mixture in a chemiluminescent reaction which comprises oxidizing the chemiluminogenic compound in the presence of an effective amount of an enhancer to obtain an enhanced chemiluminescent signal, wherein the chemiluminogenic compound is an acridinium compound, preferably an acridinium ester or an acridinium sulfonamide, wherein said enhancer is a compound or a mixture of two, three or more compounds, and wherein said enhancer compound or each of these enhancer compounds is selected from the group consisting of quarternary amine cationic substances of formula (I)

formula (I)

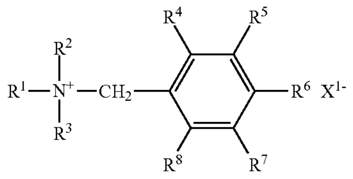

wherein $R^1$ is $C_3$-$C_{20}$ alkyl or alkenyl; and $R^2$ and $R^3$ are independently from each other $C_1$-$C_4$ alkyl or alkenyl; and $R^4$, $R^5$, $R^6$, $R^7$ and $R^8$ are independently from each other hydrogen, alkyl, alkenyl; and $X^{1-}$ is halogenide or hydroxyl-ion, preferably chloride or bromide.

The effective amount of enhancer according to the present invention is provided by one, two or more enhancer compounds wherein each of them is selected from the group consisting of quarternary amine cationic substances of formula (I) as disclosed herein.

Each enhancer compound according to the present invention has an aromatic head group. A possible anionic counterion of the cationic part of an enhancer compound according to the present invention includes but is not limited to chloride, bromide and hydroxide.

DETAILED DESCRIPTION OF THE INVENTION

Figure 1:
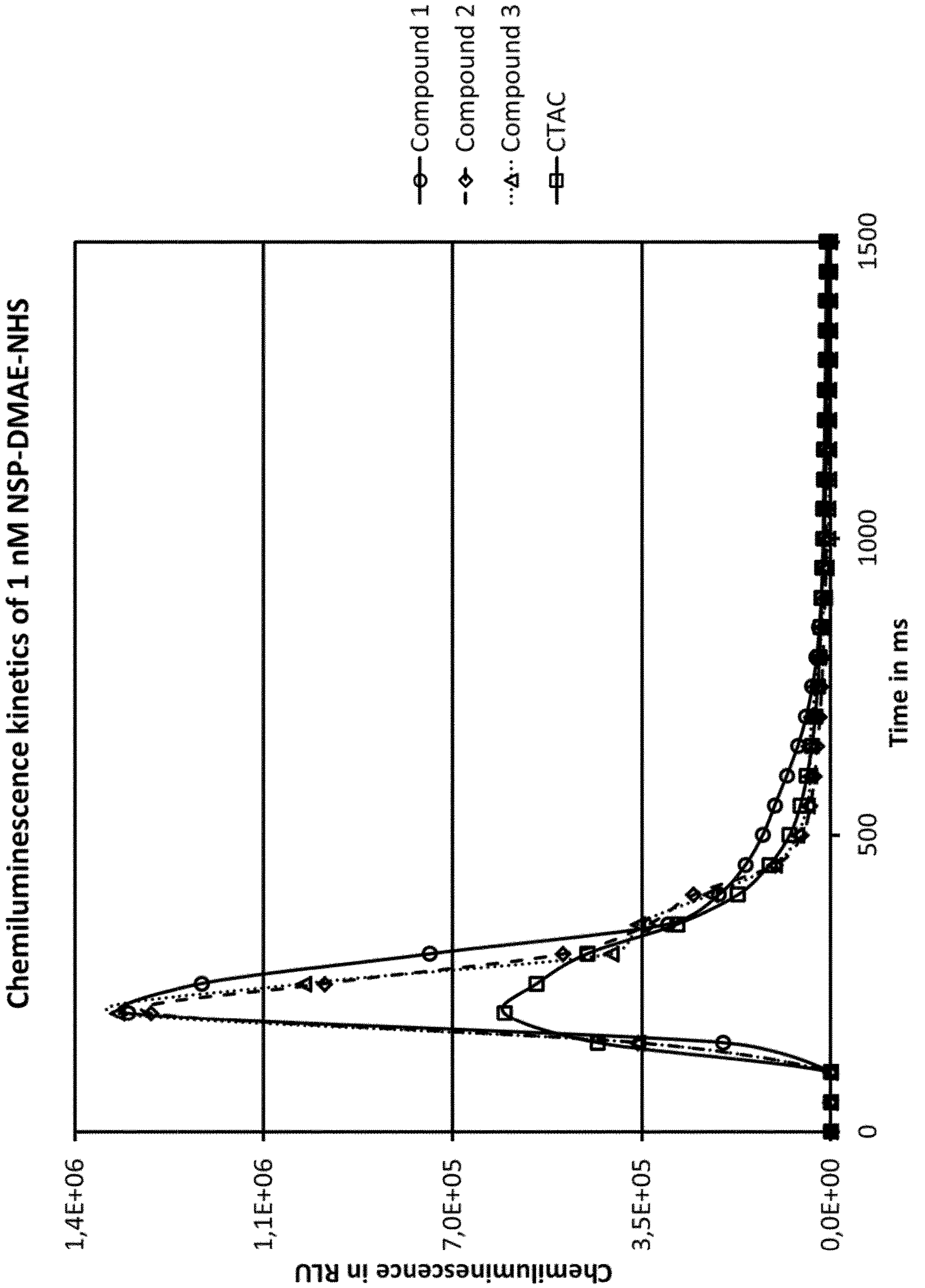
FIG. 1 shows the chemiluminescence kinetics of 1 nM NSP-DMAE-NHS in the presence of 0.5% (w/v) of three different cationic compounds, each with an aromatic head group (compound 1: Benzyldimethylhexadecylammonium chloride; compound 2: Benzalkonium chloride; compound 3: Alkyl ($C_{12}$-$C_{14}$) dimethylethylbenzyl-ammonium chloride) or in the presence of 0.5% (w/v) of the cationic compound CTA C lacking an aromatic head group.

In a preferred embodiment, the method according to the present invention includes the step of adding the enhancer to a chemiluminescent reaction mixture containing the chemiluminogenic compound, i.e. the acridinium compound e.g. the acridinium ester or the acridinium sulfonamide.

In a preferred embodiment, the enhancer compound or each of the enhancer compounds according to the present invention is or are selected from the group consisting of quarternary amine cationic substances of formula (I) as disclosed herein, wherein $R^1$ is $C_3$-$C_{18}$ alkyl or alkenyl, preferably $C_5$-$C_{18}$ alkyl or alkenyl; more preferably $C_8$-$C_{16}$ alkyl or alkenyl; most preferably $C_{12}$-$C_{14}$ alkyl or alkenyl; $R^2$ and $R^3$ are independently from each other methyl, ethyl, propyl or butyl, preferably methyl; $R^4$, $R^5$, $R^6$, $R^7$ and $R^8$ are independently from each other hydrogen, alkyl, alkenyl, preferably hydrogen, methyl or ethyl; and/or $X^{1-}$ is chloride or bromide, preferably chloride.

In a preferred embodiment, the enhancer compound, at least one compound of the enhancer or each compound of the enhancer according to the present invention is selected from the group consisting of Benzyldimethylicosylammonium chloride,
Benzyldimethylnonadecylammonium chloride,
Benzyldimethyloctadecylammonium chloride,
Benzyldimethylheptadecylammonium chloride,
Benzyldimethylhexadecylammonium chloride,
Benzyldimethylpentadecylammonium chloride,
Benzyldimethyltetradecylammonium chloride,
Benzyldimethyltridecylammonium chloride,
Benzyldimethyldodecylammonium chloride,
Benzyldimethylundecylammonium chloride,
Benzyldimethyldecylammonium chloride,
Benzyldimethylnonylammonium chloride,
Benzyldimethyloctylammonium chloride,
Benzalkonium chloride,
Benzyldimethylheptylammonium chloride,
Benzyldimethylhexylammonium chloride,
Benzyldimethylpentylammonium chloride,
Benzyldimethylbutylammonium chloride,
Benzyldimethylpropylammonium chloride,
Benzyltripropylammonium chloride,
Benzyldipropylethylammonium chloride,
Benzyldiethylpropylammonium chloride,
Benzyldipropylmethylammonium chloride,
Benzylpropylethylmethylammonium chloride,
Benzyltributylammonium chloride,
Benzyldibutylpropylammonium chloride,
Benzyldipropylbutylammonium chloride,
Benzylbutylpropylethylammonium chloride,
Benzylbutylpropylmethylammonium chloride,
Benzylbutylethylmethylammonium chloride,
Benzyldiethylbutylammonium chloride,
$C_{12-14}$-alkyldimethyl (ethylbenzyl) ammonium chloride,
Dodecyl (ethylbenzyl) dimethylammonium chloride,
Tetradecyldimethyl (ethylbenzyl) ammonium chloride,
Octadecyldimethyl (ar-ethylbenzyl) ammonium chloride and the respective aforementioned compounds containing bromide instead of chloride.

A list of exemplary enhancer compounds including the molecular structure according to the present invention (cationic substances with aromatic head groups suitable as chemiluminescence enhancer) is presented in Table 1. To clarify the identity of the listed substances despite possible ambiguities in chemical nomenclature the Chemical Abstracts Service (CAS) registry numbers and/or Compound records (CID) are listed in Table 1, if this information could be found and was publicly available. CAS registry numbers according to the Division of the American Chemical Society are accessible via https://www.cas.org or https://commonchemistry.cas.org. CID records can be found in the PubChem database of the National Institutes of Health via https://pubchem.ncbi.nlm.nih.gov. If no CAS and/or no CID were assigned to a compound or no information was publicly available the respective compound was defined as "n.d.".

TABLE 1

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$ | | | | | | Molecular structure of suitable chemiluminescence enhancer (Cationic part plus anionic counterion $X^{1-}$) |
|---|---|---|---|---|---|---|---|
| | Chloride | | Bromide | | Hydroxide | | |
| | CAS | CID | CAS | CID | CAS | CID | |
| Benzyldimethylicosylammonium | 37557-89-4 | 37781 | 25271-92-5 | 21666128 | n.d. | 88777875 | 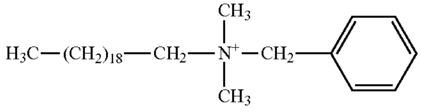 $X^{1-}$ |
| Benzyldimethylnonadecylammonium | 16576-99-1 | 14367850 | 2367044-60-6 | 141364238 | n.d. | n.d | 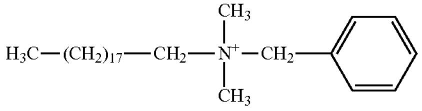 $X^{1-}$ |
| Benzyldimethyloctadecylammonium | 122-19-0 | 31204 | 22546-65-2 | 10479761 | 19493-24-4 | 13650437 | 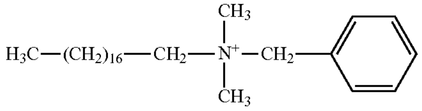 $X^{1-}$ |
| Benzyldimethylheptadecylammonium | 16576-98-0 | 3014947 | 1098301-66-6 | 87844792 | n.d. | n.d. | 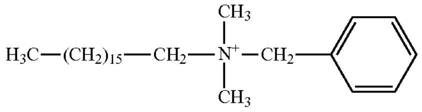 $X^{1-}$ |
| Benzyldimethylhexadecylammonium | 122-18-9 | 31202 | 3529-04-2 | 165133 | 54942-73-3 | 12986409 | 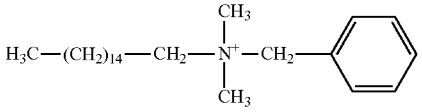 $X^{1-}$ |
| Benzyldimethylpentadecylammonium | 16576-96-8 | 3014945 | 860534-71-0 | 87844402 | n.d. | n.d. | 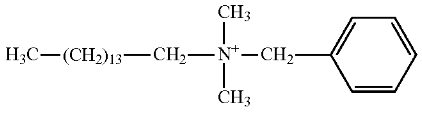 $X^{1-}$ |

TABLE 1-continued

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$ | | | | | | Molecular structure of suitable chemiluminescence enhancer (Cationic part plus anionic counterion $X^{1-}$) |
|---|---|---|---|---|---|---|---|
| | Chloride | | Bromide | | Hydroxide | | |
| | CAS | CID | CAS | CID | CAS | CID | |
| Benzyldimethyltetradecylammonium | 139-08-2 | 8755 | 18773-88-1 | 9866364 | 75169-64-1 | 12940063 | 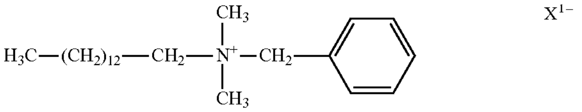 |
| Benzyldimethyltridecylammonium | 1641-93-6 | 3014024 | 136816-61-0 | 85616532 | 2304352-54-1 | 88254963 | 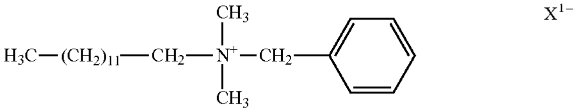 |
| Benzyldimethyldodecylammonium | 139-07-1 | 8753 | 7281-04-1 | 23705 | 500-33-4 | 12300039 | 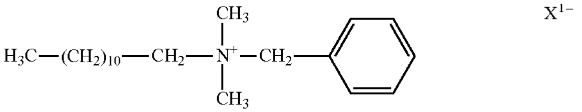 |
| Benzyldimethylundecylammonium | 16576-95-7 | 14029537 | 776331-80-7 | 86005046 | 1429485-54-0 | n.d. | 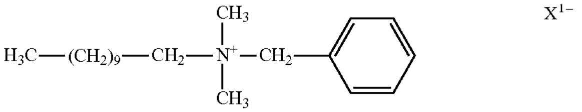 |
| Benzyldimethyldecylammonium | 965-32-2 | 13762 | 32014-84-9 | 11660400 | 1429485-00-6 | 13650436 | 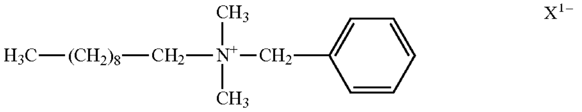 |
| Benzyldimethylnonylammonium | 3024-71-3 | 23275523 | 73620-02-7 | 71402097 | 1429485-31-3 | n.d | 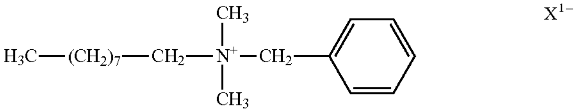 |
| Benzyldimethyloctylammonium | 959-55-7 | 13740 | 58965-50-7 | 15636465 | 1929613-88-6 | 13650435 | 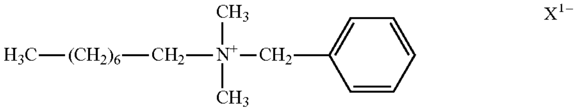 |

TABLE 1-continued

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$: Chloride CAS | Chloride CID | Bromide CAS | Bromide CID | Hydroxide CAS | Hydroxide CID | Molecular structure of suitable chemiluminescence enhancer (Cationic part plus anionic counterion $X^{1-}$) | |
|---|---|---|---|---|---|---|---|---|
| Benzyldimethylheptylammonium | 33296-72-9 | 23274918 | 77339-31-2 | 87776931 | n.d. | n.d. | 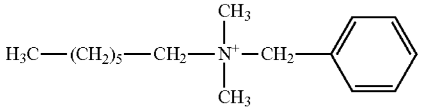 | $X^{1-}$ |
| Benzyldimethylhexylammonium | 22559-57-5 | 23274630 | 58965-49-4 | 71443268 | 1627560-59-1 | 88006571 | 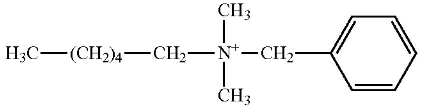 | $X^{1-}$ |
| Benzyldimethylpentylammonium | 54335-04-5 | 13086197 | 1098023-81-4 | 87777946 | n.d. | 88778049 | 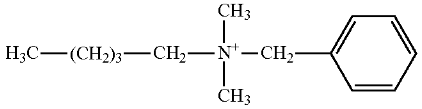 | $X^{1-}$ |
| Benzyldimethylbutylammonium | 72617-58-4 | 21988052 | 58965-48-3 | 71443269 | n.d. | n.d. | 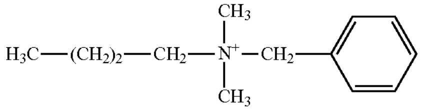 | $X^{1-}$ |
| Benzyldimethylpropylammonium | 87314-55-4 | 23273922 | 54884-45-6 | 71364434 | n.d. | 88159092 | 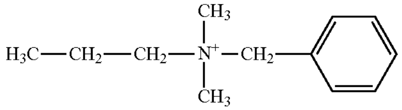 | $X^{1-}$ |
| Benzyltripropylammonium | 5197-87-5 | 6097067 | 5350-75-4 | 13056170 | 119496-03-6 | 18413460 | 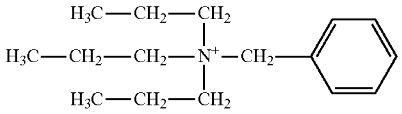 | $X^{1-}$ |
| Benzyldipropylethylammonium | 5197-84-2 | 88318157 | 90105-60-5 | 71430311 | n.d. | 88318143 | 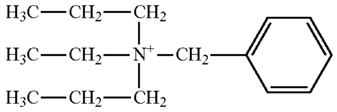 | $X^{1-}$ |

TABLE 1-continued

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$ Chloride CAS | Chloride CID | Bromide CAS | Bromide CID | Hydroxide CAS | Hydroxide CID | Molecular structure of suitable chemiluminescence enhancer (Cationic part plus anionic counterion $X^{1-}$) |
|---|---|---|---|---|---|---|---|
| Benzyldiethylpropylammonium | 5197-83-1 | 22768269 | n.d. | n.d. | n.d. | 88317889 | 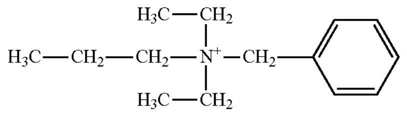 $X^{1-}$ |
| Benzyldipropylmethylammonium | n.d. | 121302550 | 90105-59-2 | 71430312 | 1627560-55-7 | n.d. | 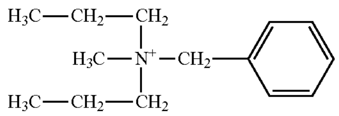 $X^{1-}$ |
| Benzylpropylethylmethylammonium | 5197-85-3 | 88317176 | 96200-25-8 | n.d. | n.d. | 88317794 | 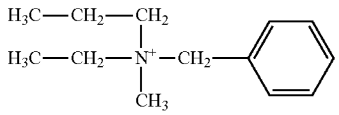 $X^{1-}$ |
| Benzyltributylammonium | 23616-79-7 | 159952 | 25316-59-0 | 2724282 | 27574-41-0 | 22149663 | 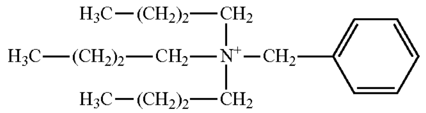 $X^{1-}$ |
| Benzyldibutylpropylammonium | n.d. | n.d. | n.d. | n.d. | n.d. | n.d. | 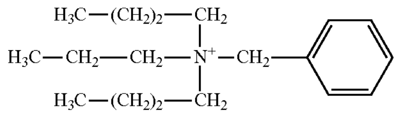 $X^{1-}$ |
| Benzyldipropylbutylammonium | n.d. | n.d. | 90105-61-6 | 71430309 | n.d. | n.d. | 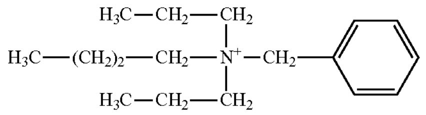 $X^{1-}$ |
| Benzylbutylpropylethylammonium | n.d | n.d. | n.d. | n.d. | n.d. | n.d. | 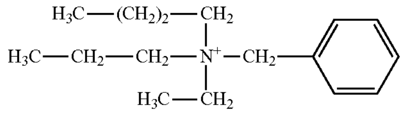 $X^{1-}$ |

TABLE 1-continued

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$ | | | | | | Molecular structure of suitable chemiluminescence enhancer (Cationic part plus anionic counterion $X^{1-}$) | |
|---|---|---|---|---|---|---|---|---|
| | Chloride | | Bromide | | Hydroxide | | | |
| | CAS | CID | CAS | CID | CAS | CID | | |
| Benzylbutylpropylmethylammonium | n.d. | n.d. | n.d. | n.d. | n.d. | n.d. | 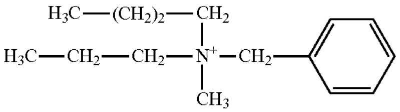 | $X^{1-}$ |
| Benzylbutylethylmethylammonium | n.d | n.d. | n.d. | n.d. | n.d. | n.d. | 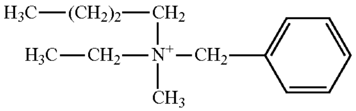 | $X^{1-}$ |
| Benzyldiethylbutylammonium | 5197-86-4 | 88317500 | 90105-68-3 | 71430302 | n.d. | 88317793 | 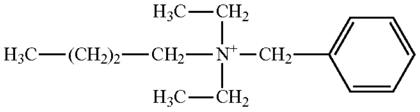 | $X^{1-}$ |
| Hexadecyldimethyl(ethylbenzyl)-ammonium | 2065159-60-4 | 122443 | n.d. | n.d. | n.d. | n.d | 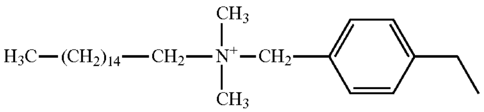 | $X^{1-}$ |
| Tetradecyldimethyl(ethylbenzyl)-ammonium | n.d. | 10157558 | n.d. | n.d. | n.d. | n.d | 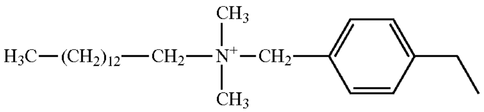 | $X^{1-}$ |
| Dodecyl(ethylbenzyl)dimethyl-ammonium | 14351-42-9 | 33917 | n.d. | n.d | n.d | n.d. | 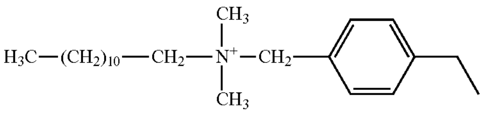 | $X^{1-}$ |
| Benzalkonium | 63449-41-2; 8001-54-5; 64365-16-8 | n.d. | 91080-29-4; 8043-47-8 | n.d. | n.d | n.d. | 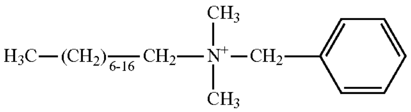 | $X^{1-}$ |

TABLE 1-continued

Exemplary list of enhancer compounds with aromatic head groups suitable as chemiluminescence enhancer according to the present invention. Possible counterions of the cationic parts of the compounds include but are not limited to chloride, bromide and hydroxide, the latter of which are shown in the table.

| Cationic part of compound suitable as chemiluminescence enhancer | Anionic counterion $X^{1-}$ | | | | | | Molecular structure of suitable chemiluminescence enhancer (Cationic part plus anionic counterion $X^{1-}$) |
|---|---|---|---|---|---|---|---|
| | Chloride | | Bromide | | Hydroxide | | |
| | CAS | CID | CAS | CID | CAS | CID | |
| $C_{12-14}$-alkyldimethyl(ethylbenzyl)-ammonium | 85409-23-0 | n.d. | n.d. | n.d | n.d. | n.d. | 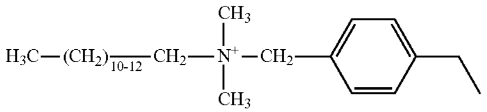 $X^{1-}$ |

The enhancer according to the present invention may constitute of a mixture of two, three or more of the aforementioned compounds in Table 1 and this mixture may also be commercially available as an individual article. One example for a mixture of two, three or more of the aforementioned compounds in Table 1, which is commercially available as an individual article is e.g. Benzalkonium chloride or Benzalkonium bromide. Benzalkonium chloride is a mixture of alkylbenzyldimethylammonium chlorides (ABDAC), the alkyl part of which consists of $C_8$ to $C_{18}$ chains. Depending on the composition of the mixture multiple commercial articles and CAS numbers can be found for Benzalkonium chloride, respectively.

If an enhancer compound according to the present invention includes a chiral C atom, the enhancer compound discloses and includes all isomer forms of said compound.

In a preferred embodiment, the effective amount of said enhancer in the chemiluminescent reaction mixture is 0.001% by weight per volume (w/v) or greater, preferably 0.01% by w/v, more preferably 0.1% by w/v or greater, most preferably 0.2% by w/v or greater, in each case based on the total volume of the chemiluminescent reaction mixture. In general, the effective amount of enhancer necessary to enhance the chemiluminescent signal of the chemiluminogenic compound in the chemiluminescent reaction mixture in the chemiluminescent reaction will vary depending on the enhancer chosen and may be determined empirically. As a general rule, an effective amount of enhancer in a chemiluminescent reaction mixture is greater than 0.005% by weight per volume, preferably greater than 0.01% by w/v, in each case based on the total volume of the chemiluminescent reaction mixture. In a preferred embodiment the amount of the enhancer to effect an enhanced chemiluminescent signal included in a chemiluminescent reaction mixture is in the range of 0,005% by w/v to 3% by w/v, preferably in the range of 0,01% by w/v to 2% by w/v, also preferably in the range of 0.05% by w/v to 1% by w/v, more preferably in the range of 0,08% by w/v to 0,8% by w/v, even more preferably in the range of 0.1% by w/v to 0,6% by w/v, most preferably in the range of 0,2% by w/v to 0.5% by w/v, in each case based on the total volume of the chemiluminescent reaction mixture. In a specifically preferred embodiment the amount of the enhancer to effect an enhanced chemiluminescent signal included in a chemiluminescent reaction mixture is in the range of 0,08% by w/v to 0,4% by w/v, in each case based on the total volume of the chemiluminescent reaction mixture.

Preferably, the chemiluminescent reaction according to a method or use of the present invention should be conducted at a temperature of from 20° C. to 37° C. and at a pH in the range of 10 to 13,5. The enhancer according to the present invention is preferably diluted prior to use in the method of this invention. Suitable diluents include water, aqueous acid solutions or aqueous basic solutions.

In a preferred embodiment, the enhancer according to the present invention is soluble in the chemiluminescent reaction mixture.

In a preferred embodiment, the method according to the present invention is performed by an immunoassay or is part of an immunoassay, wherein the immunoassay preferably comprises the step of detecting the presence or absence of an antigen, antibody or autoantibody. The immunoassay can preferably be selected from the group comprising a competitive assay, a capture bridge assay, an immunometric assay, a direct or indirect class capture assay. The principle of each of these formats is detailed in The Immunoassay Handbook, 3rd edition, edited by David Wild, Elsevier, 2005.

In a preferred embodiment, the chemiluminescent reaction according to the present invention is a flash-type chemiluminescent reaction. The flash-type chemiluminescent reaction results in a bright chemiluminescence signal in the range of seconds to minutes.

In a further preferred embodiment, the method for enhancing the chemiluminescent signal of a chemiluminogenic compound in a chemiluminescent reaction mixture in a chemiluminescent reaction according to the present invention comprises a flash-type chemiluminescent reaction as chemiluminescent reaction.

In a preferred embodiment, the enhancer according to the present invention is combined with the chemiluminogenic compound in the chemiluminescent reaction mixture before, simultaneously to or shortly after the start of the chemiluminescent reaction, preferably the enhancer is combined with the chemiluminogenic compound in the chemiluminescent reaction mixture simultaneously to the start of the chemiluminescent reaction.

In a preferred embodiment, the chemiluminescent signal generated by the chemiluminescent reaction according to the present invention is detected for a fixed duration of time, preferably, the chemiluminescent reaction mixture is formed, the chemiluminescent reaction is started and the signal is detected concurrently, more preferably the duration of the detection ranges from 0.01 to 360 seconds, even more preferably from 0.1 to 30 seconds, even more preferably from 0.3 to 15 seconds, and most preferably from 0.5 to 10 seconds, wherein in each case the duration of the detection starts with the start of the chemiluminescent reaction.

In a preferred embodiment, the method according to the present invention comprises the steps combining the enhancer according to the present invention with the chemiluminogenic compound in the chemiluminescent reaction mixture simultaneously to the start of the chemiluminescent reaction and/or detecting the chemiluminescent signal generated by the chemiluminescent reaction according to the present invention starting with the start of the chemiluminescent reaction for a fixed duration of time of from 0.1 to 10 seconds.

According to the present invention, the chemiluminescent reaction is preferably started by initiating the oxidation of the chemiluminogenic compound. Preferably, the initiating step for oxidation of the chemiluminogenic compound is performed by adding an oxidizing compound, preferably hydrogen peroxide.

In a preferred embodiment, preferably according to at least one of the preceding embodiments, the chemiluminescent reaction mixture additionally includes hydrogen peroxide, an acid, preferably nitric acid, and/or an alkaline hydroxide, preferably sodium hydroxide.

In a preferred embodiment, preferably according to at least one of the preceding embodiments, the chemiluminescent reaction mixture includes a trigger solution A and a trigger solution B. Preferably, the trigger solution A includes an acid, preferably nitric acid, and hydrogen peroxide and the trigger solution B includes an alkaline hydroxide, preferably sodium hydroxide, and the enhancer according to the invention.

In a preferred embodiment, preferably according to at least one of the preceding embodiments, the chemiluminescent reaction mixture is provided by mixing a trigger solution A, preferably including nitric acid and hydrogen peroxide, and a trigger solution B, preferably including sodium hydroxide and the enhancer according to the invention, with the chemiluminogenic compound, which is an acridinium compound, preferably an acridinium ester or an acridinium sulfonamide.

The chemiluminogenic compound according to the present invention is an acridinium compound, preferably an acridinium ester or an acridinium sulfonamide.

It is well known in the art, that acridinium compounds exist in an equilibrium between the acridinium form and the pseudo-base form in aqueous media where virtually all immunoassays are performed. The pseudo-base form of acridinium compounds cannot react with hydrogen peroxide and thus cannot produce chemiluminescence. The equilibrium between the chemiluminescent acridinium form and non-chemiluminescent pseudo-base form is strongly influenced by the pH of the medium. Acidic pH promotes the formation of the acridinium form and basic pH promotes the formation of the pseudo-base form.

In heterogeneous assay formats, chemiluminescence from acridinium compounds or acridinium compound-labeled biologically active molecules, referred to as tracers or conjugates, is normally triggered by the sequential addition of two reagents. An initial treatment of the acridinium compound with a strong acid containing peroxide is necessary to convert the pseudo-base form of acridinium compounds to the acridinium form. The subsequent treatment with alkali solution then neutralizes the acid and raises the pH of the reaction medium for the ionization of hydrogen peroxide to allow light emission to take place.

Preferably, the chemiluminogenic compound used in the present invention is an acridinium ester according to formula (II):

formula (II)

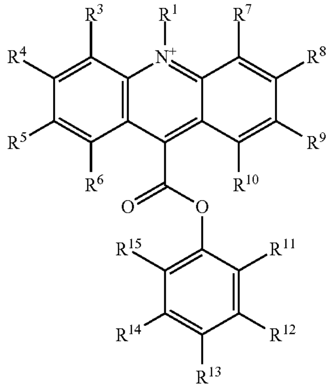

wherein $R^1$ is an alkyl, alkenyl, alkynyl, aryl or aralkyl, sulfoalkyl, carboxyalkyl and oxoalkyl; and wherein $R^3$ through $R^{15}$ are each independently from each other selected from the group consisting of hydrogen, alkyl, alkenyl, alkynyl, aryl or aralkyl, amino, amido, acyl, alkoxyl, hydroxyl, carboxyl, halogen, halogenide, nitro, cyano, sulfo, sulfoalkyl, sulfamoyl, carboxyalkyl, succinimidyl ester and oxoalkyl or any other leaving group; and optionally, if present, $X^{1-}$ is an anion;

or an acridinium sulfonamide according to formula (III)

formula (III)

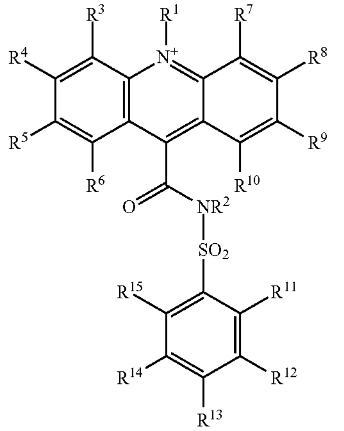

wherein $R^1$ is selected from the group consisting of alkyl, alkenyl, alkynyl, aryl or aralkyl, sulfoalkyl, carboxyalkyl and oxoalkyl and wherein $R^2$ through $R^{15}$ are each independently from each other selected from the group consisting of hydrogen, alkyl, alkenyl, alkynyl, aryl or aralkyl, amino, amido, acyl, alkoxyl, hydroxyl, carboxyl, halogen, halogenide, nitro, cyano, sulfo, sulfoalkyl, sulfamoyl, carboxyalkyl, succinimidyl ester and oxoalkyl or any other leaving group; and optionally, if present, $X^{1-}$ is an anion.

In a preferred embodiment, preferably according to at least one of the preceding embodiments, the chemiluminogenic compound is an acridinium ester according to formula (II) as disclosed herein, wherein additionally $R^{12}$ and $R^{14}$ are each independently from each other selected from the group consisting of: hydrogen, alkyl, amino, carboxyl, hydroxyl, alkoxyl, nitro, or halogenide; $R^{11}$ and $R^{15}$ are each independently from each other selected from the group consisting of hydrogen, alkyl, alkenyl, alkynyl, aryl, alkoxyl, amino, amido, sulfonamide or sulfide; and $R^{13}$ represents the following substituent $$R^{13}{=}L{-}R^{16}{-}R^{17}$$

wherein L is sulfamoyl or omitted, $R^{16}$ is omitted or is alkyl, aryl, aralkyl, (amido) z with z=1-10, preferably z=1 or 2, or (polyethylene oxide), with x=1-10, preferably x=4; and $R^{17}$ is selected from the group consisting of:

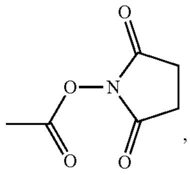
,
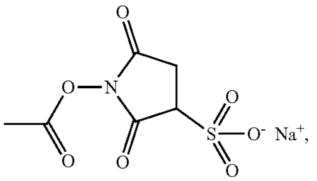

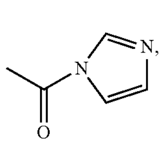

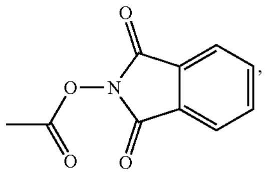

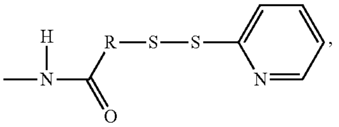

-continued

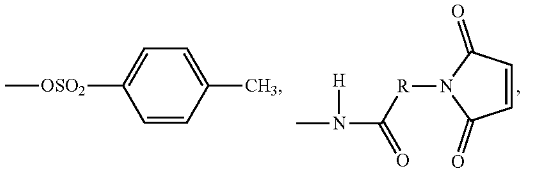

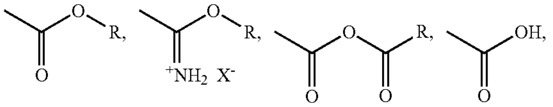

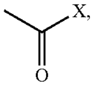 —N=C=S, —OSO$_2$F, —N=C=O,

—OSO$_2$CF$_3$, —OSO$_2$C$_4$F$_9$, —NH$_2$, —H, —N$_2^+$ X,

—halide, —N$_3$, 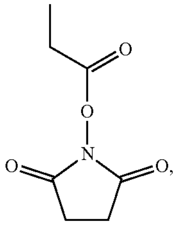

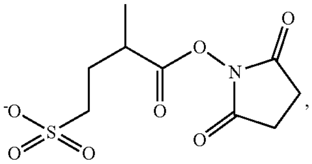

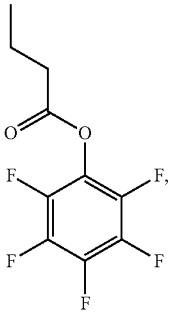

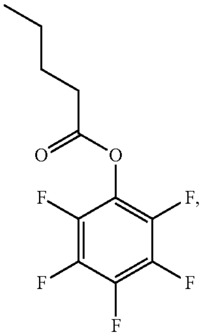

$SO_2Cl$ or any other leaving group, wherein R is alkyl, aryl, or aralkyl; X is $CH_3SO_4$, $OSO_2F$, halogenide, $OSO_2CF_3$, $OSO_2C_4F_9$, or

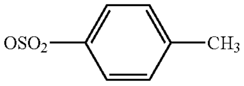

and wherein $R^{12}$, $R^{13}$ and $R^{14}$ substituent positions are interchangeable.

In a preferred embodiment, preferably according to at least one of the preceding embodiments, the chemiluminogenic compound is an acridinium sulfonamide according to formula (III) as disclosed herein, wherein additionally $R^{12}$, $R^{13}$ and $R^{14}$ are each independently from each other selected from the group consisting of hydrogen, alkyl, amino, carboxyl, hydroxyl, alkoxyl, nitro, or halogenide; $R^{11}$ and $R^{15}$ are each independently from each other selected from the group consisting of hydrogen, alkyl, alkenyl, alkynyl, aryl, alkoxyl, amino, amido, sulfonamide or sulfide; and $R^2$ represents the following substituent $$R^2{=}L{-}R^{16}{-}R^{17}$$

wherein L is sulfamoyl or omitted, $R^{16}$ is omitted or is alkyl, aryl, aralkyl, $(\text{amido})_z$ with z=1-10, preferably z=1 or 2, or (polyethylene oxide), with x=1-10, preferably x=4; and $R^{17}$ is selected from the group consisting of

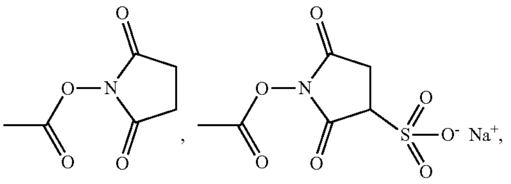

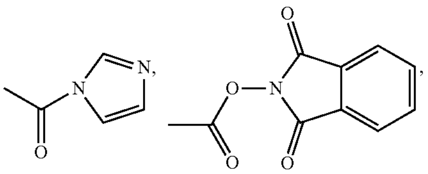

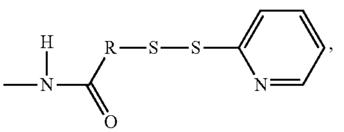

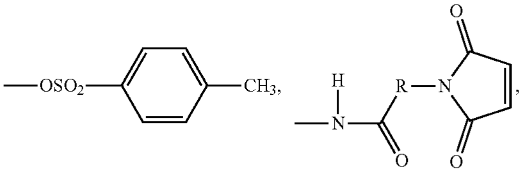

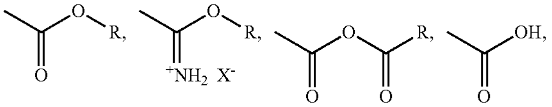

-continued

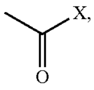 $—N{=}C{=}S$, $—OSO_2F$, $—N{=}C{=}O$,

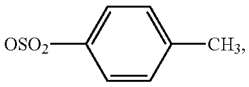

$—OSO_2CF_3$, $—OSO_2C_4F_9$, $—NH_2$, $—H$, $—N_2^+X$,

—halide, $—N_3$, 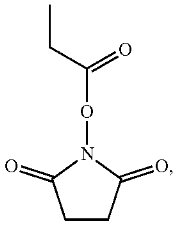

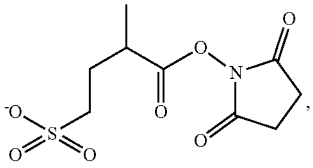, 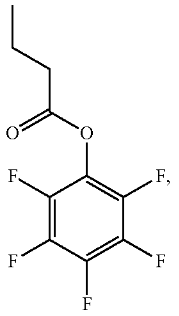

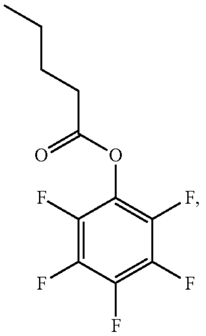

$SO_2Cl$ or any other leaving group, wherein R is alkyl, aryl, or aralkyl; X is $CH_3SO_4$, $OSO_2F$, halogenide, $OSO_2CF_3$, $OSO_2C_4Fe$, or and wherein $R^{11}$ through $R^{15}$ substituent positions are interchangeable.

Acridinium compounds which are useful in the present invention are further described in U.S. Application Ser. No. 915,527, filed Oct. 6, 1986 and in Natrajan et al., "A comparison of chemiluminescent acridinium dimethylphenyl ester labels with different conjugation sites", Org Biomol Chem, 13 (9): 2622-337, March 2015.

In a preferred embodiment, preferably according to at least one of the preceding embodiments, the chemiluminogenic compound is selected from the group consisting of N-sulfopropyl-dimethylacridinium-(polyethylene oxide),-N-hydroxysuccinimide ester (NSP-DMAE-PEOx-NHS) with x=1-10, preferably N-sulfopropyl-dimethylacridinium-(polyethylene oxide) 4-N-hydroxysuccinimide ester (NSP-DMAE-PEO4-NHS);

2,6-(dimethyl)-3-chlorosulfonylphenyl-N-(3-sulfopropyl)-acridinium-9-carboxylate (SPAE);

2,6-(dimethyl)-3-sulfamoylphenyl-N-(3-sulfopropyl)-acridinium-9-carboxylate-(polyethyleneoxide) 4-pentafluorophenyl ester (SPAE-PEO4-PFP);

2,6-(dimethyl)-3-chlorosulfonylphenyl-N-methyl-acridinium-9-carboxylate triflate (MeAE);

2,6-(dimethyl)-3-sulfamoylphenyl-N-methyl-acridinium-9-carboxylate triflate-(polyethylene oxide) 4-N-hydroxysuccinimide ester (MeAE-PEO4-NHS), 2,3,4,5,6-pentafluorophenyloxy-1-carbonyl-4,7, 10,13-tetraoxapentade-cyl-(15-amino)-3'-sulfonyl-2',6'-dimethylphenyl-N-(3-sulfopropyl)-acridinium-9-carboxylate, 10-Methyl-2,6-dimethyl-acridinium-NHS ester methylsulfate (Me-DMAE-NHS)

N-sulfopropyl-dimethylacridinium-N-hydroxysuccinimide (NSP-DMAE-NHS); and

N-sulfopropyl-acridinium-sulfonamide-N-hydroxysuccinimide (NSP-SA-NHS).

A list of exemplary acridinium compounds according to formula (II) or (III) as defined herein, suitable as chemiluminogenic compounds according to the present invention is presented in Table 2. To clarify the identity of the listed substances despite possible ambiguities in chemical nomenclature the Chemical Abstracts Service (CAS) registry numbers and/or Compound records (CID) are listed in Table 2, if this information could be found and was publicly available. CAS registry numbers according to the Division of the American Chemical Society are accessible via https://www.cas.org or https://commonchemistry.cas.org. CID records can be found in the PubChem database of the National Institutes of Health via https://pubchem.ncbi.nlm.nih.gov. If no CAS and/or no CID were assigned to a compound or no information was publicly available the respective compound was defined as "n.d.".

TABLE 2

Exemplary list of acridinium compounds according to formula (II) or (III) according to the present invention.

| Acridinium compound | CAS | CID | IUPAC name | Molecular structure of acridinium compound |
|---|---|---|---|---|
| Me-DMAE-NHS | 115853-74-2 | 14153946 | [4-(2,5-dioxopyrrolidin-1-yl)oxycarbonyl-2,6-dimethylphenyl] 10-methylacridin-10-ium-9-carboxylate; methyl sulfate | 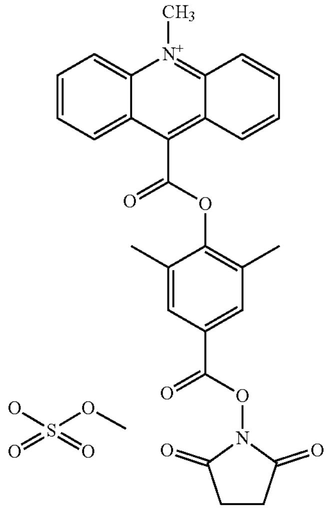 |
| NSP-DMAE-NHS | 194357-64-7 | 20608334 | 3-[9-[4-(2,5-dioxopyrrolidin-1-yl)oxycarbonyl-2,6-dimethylphenoxy] carbonylacridin-10-ium 10-yl]propane-1-sulfonate | 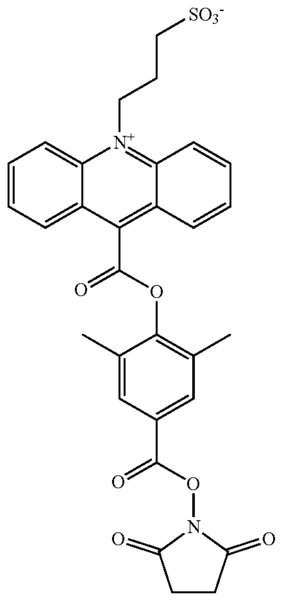 |

TABLE 2-continued

| Exemplary list of acridinium compounds according to formula (II) or (III) according to the present invention. | | | | |
|---|---|---|---|---|
| Acridinium compound | CAS | CID | IUPAC name | Molecular structure of acridinium compound |
| NSP-SA-NHS | 199293-83-9 | 59642932 | 3-[9-[[4-(2,5-dioxopyrrolidin-1-yl)oxy-4-oxobutyl]-(4-methylphenyl) sulfonylcarbamoyl]acridin-10-ium-10-yl]propane-1-sulfonate | 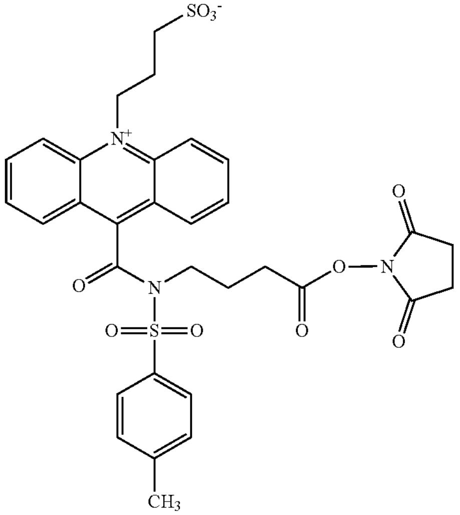 |
| Me-DMAE-PEO4-NHS | 663921-17-3 | 20818504 | [3-[2-[2-[2-[2-[3-(2,5-dioxopyrrolidin-1-yl)oxy-3-oxopropoxy]ethoxy]ethoxy]ethoxy] ethylsulfamoyl]-2,6-dimethylphenyl] 10-methylacridin-10-ium-9-carboxylate | 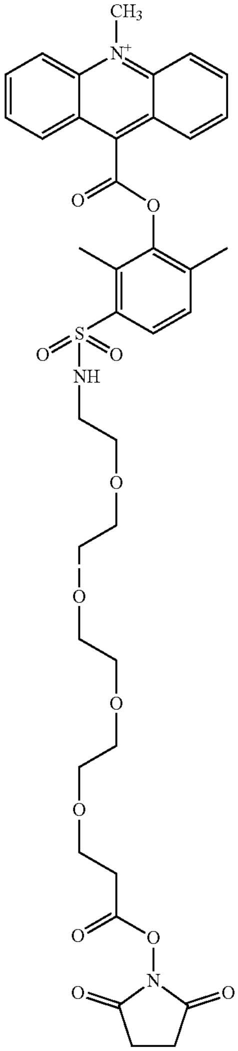 [SMILES: Cc1ccc(S(=O)(=O)NCCOCCOCCOCCOCCC(=O)ON2C(=O)CCC2=O)c(C)c1OC(=O)c1c2ccccc2[n+](C)c2ccccc12] |

TABLE 2-continued

Exemplary list of acridinium compounds according to formula (II) or (III) according to the present invention.

| Acridinium compound | CAS | CID | IUPAC name | Molecular structure of acridinium compound |
|---|---|---|---|---|
| MeAE-HCA-NHS | 664351-78-4 | 20818505 | 3-[[2,4-Dimethyl-3-(10-methylacridin-10-ium-9-carbonyl)oxyphenyl] sulfonylamino]-4-(2,5-dioxopyrrolidin-1-yl)oxy-4-oxobutane-1-sulfonate | 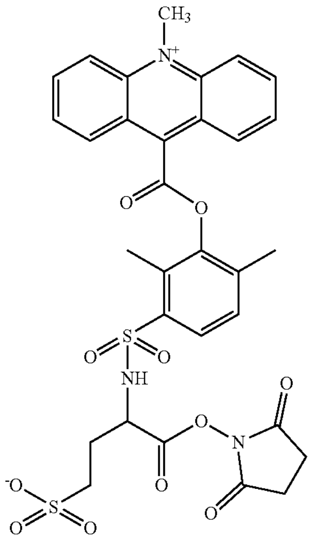 |
| MeAE-Gly3-NHS | 663921-23-1 | 20818507 | [3-[[2-[[2-[[2-(2,5-dioxopyrrolidin-1-yl)oxy)-2-oxoethyl]amino]-2-oxoethyl]amino]-2-oxoethyl] sulfamoyl]-2,6-dimethylphenyl] 10-methylacridin-10-ium-9-carboxylate | 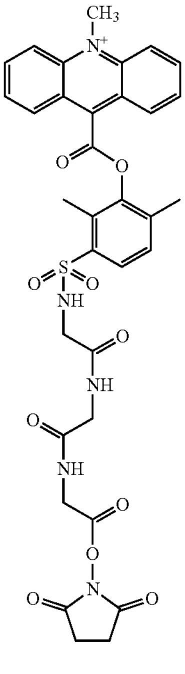 [SMILES: Cc1ccc(S(=O)(=O)NCC(=O)NCC(=O)NCC(=O)ON2C(=O)CCC2=O)c(C)c1OC(=O)c1c2ccccc2[n+](C)c2ccccc12] |

TABLE 2-continued

Exemplary list of acridinium compounds according to formula (II) or (III) according to the present invention.

| Acridinium compound | CAS | CID | IUPAC name | Molecular structure of acridinium compound |
| --- | --- | --- | --- | --- |
| MeAE-Gly2-NHS | 663921-21-9 | 20818508 | [3-[[2-[[2-(2,5-dioxopyrrolidin-1-yl) oxy)-2-oxoethyl]amino]-2-oxoethyl] sulfamoyl]-2,6-dimethylphenyl] 10-methylacridin-10-ium-9-carboxylate | 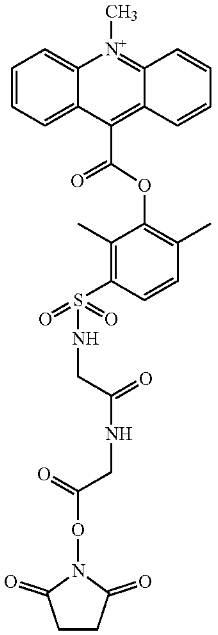 [SMILES: Cc1ccc(S(=O)(=O)NCC(=O)NCC(=O)ON2C(=O)CCC2=O)c(C)c1OC(=O)c1c2ccccc2[n+](C)c2ccccc12] |
| Me-SA-PhAc-NHS | 125603-37-4 | 19598396 | (2,5-dioxopyrrolidin-1-yl) 2-[4-[(10-methylacridin-10-ium-9-carbonyl)-(4-methylphenyl) sulfonylamino]phenyl]acetate | 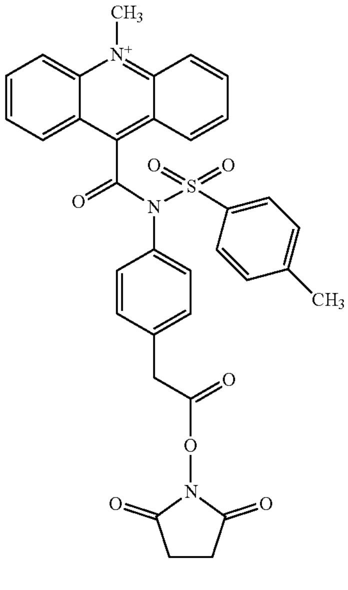 [SMILES: Cc1ccc(S(=O)(=O)N(C(=O)c2c3ccccc3[n+](C)c3ccccc23)c2ccc(CC(=O)ON3C(=O)CCC3=O)cc2)cc1] |

TABLE 2-continued

Exemplary list of acridinium compounds according to formula (II) or (III) according to the present invention.

| Acridinium compound | CAS | CID | IUPAC name | Molecular structure of acridinium compound |
|---|---|---|---|---|
| SPAE | 663921-11-7 | 20818511 | 3-[9-(3-chlorosulfonyl-2,6-dimethylphenoxy)carbonylacridin-10-ium-10-yl]propane-1-sulfonate | 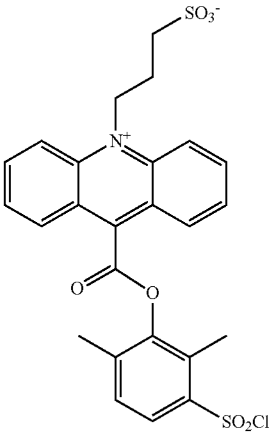 |
| SPAE-PEO4-PFP | 663921-24-2 | 20818509 | 3-[9-[2,6-dimethyl-3-[2-[2-[2-[2-[3-oxo-3-(2,3,4,5,6-pentafluorophenoxy)propoxy]ethoxy]ethoxy]ethoxy]ethylsulfamoyl]phenoxy]carbonylacridin-10-ium-10-yl]propane-1-sulfonate | 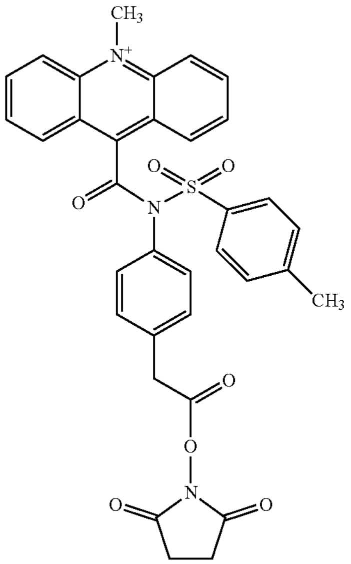 [SMILES: Cc1ccc(S(=O)(=O)N(C(=O)c2c3ccccc3[n+](C)c3ccccc23)c2ccc(CC(=O)ON3C(=O)CCC3=O)cc2)cc1] |

The acridinium compound according to the present invention can be oxidized by any oxidant which reacts with the compound to cause excitation of the compound so that the compound emits light in a chemiluminescent reaction. A preferred oxidant is hydrogen peroxide in dilute alkali.

In a preferred embodiment, the chemiluminescent reaction mixture according to the present invention includes an oxidant in an amount of from 0.01% to 1% by volume based on the total volume of the chemiluminescent reaction mixture, preferably from 0.05% to 0.5% by volume based on the total volume of the chemiluminescent reaction mixture and most preferably from 0.1% to 0.3% by volume based on the total volume of the chemiluminescent reaction mixture.

The light emitted can be quantified using a standard measuring device such as a LB 960 Centro Microplate Luminometer (Berthold Technologies Gmbh & Co. KG, Germany), a Model 810 Luminometer (Ciba-Corning Diagnostics Corp., Medfield, MA) or a RA Analyzer 10 (Euroimmun, a PerkinElmer company, Germany).

In a preferred embodiment, the chemiluminogenic compound capable of chemiluminescence emission emits luminescence with a wavelength of 400 nm or more, preferably 400 nm to 690 nm, more preferably 400 nm to 550 nm, more preferably 405 nm to 500 nm and most preferably 410 to 490 nm.

In a $2^{nd}$ aspect, the problem underlying the present invention is solved by a use of a compound selected from the group consisting of quarternary amine cationic substances of formula (I)

formula (I)

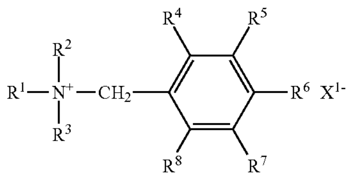

wherein $R^1$ is $C_3$-$C_{20}$ alkyl or alkenyl; and $R^2$ and $R^3$ are independently from each other $C_1$-$C_4$ alkyl or alkenyl;

and $R^4$, $R^5$, $R^6$, $R^7$ and $R^8$ are independently from each other hydrogen, alkyl, alkenyl; and $X^{1-}$ is halogenide or hydroxyl-ion, preferably chloride or bromide, for enhancing the chemiluminescent signal of an acridinium compound, preferably an acridinium ester or an acridinium sulfonamide, more preferably according to the present invention, in a chemiluminescent reaction, preferably in a chemiluminescent immunoassay.

In a preferred embodiment, the compound is selected from the group consisting of quarternary amine cationic substances of formula (I) as defined herein, wherein $R^1$ is $C_3$-$C_{18}$ alkyl or alkenyl, preferably $C_5$-$C_{18}$ alkyl or alkenyl; more preferably $C_8$-$C_{16}$ alkyl or alkenyl; most preferably $C_{12}$-$C_{14}$ alkyl or alkenyl; $R^2$ and $R^3$ are independently from each other methyl, ethyl, propyl or butyl, preferably methyl, $R^4$, $R^5$, $R^6$, $R^7$ and $R^8$ are independently from each other hydrogen, alkyl, alkenyl, preferably hydrogen, methyl or ethyl; and/or $X^{1-}$ is chloride or bromide, preferably chloride.

Preferably, one, two or more compounds selected from the group consisting of quarternary amine cationic substances of formula (I) as disclosed above are used for enhancing the chemiluminescent signal of a chemiluminogenic compound, preferably an acridinium ester or an acridinium sulfonamide, preferably according to the present invention, in a chemiluminescent reaction, preferably in a chemiluminescent immunoassay.

According to the present invention, the compound is an enhancer compound according to the present invention which has an aromatic head group.

In a $3^{rd}$ aspect, the problem underlying the present invention is solved by a chemiluminescent composition containing at least one compound selected from the group consisting of quarternary amine cationic substances of formula (I)

formula (I)

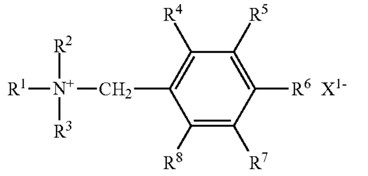

wherein $R^1$ is $C_3$-$C_{20}$ alkyl or alkenyl; and $R^2$ and $R^3$ are independently from each other $C_1$-$C_4$ alkyl or alkenyl; and $R^4$, $R^5$, $R^6$, $R^7$ and $R^8$ are independently from each other hydrogen, alkyl, alkenyl; and $X^{1-}$ is halogenide or hydroxyl-ion, preferably chloride or bromide, and at least one chemiluminogenic compound, wherein the chemiluminogenic compound is an acridinium compound, preferably an acridinium ester or an acridinium sulfonamide, more preferably an acridinium ester or an acridinium sulfonamide of formula (II) or formula (III) as disclosed herein.

According to the present invention, at least one compound in the chemiluminescent composition according to the present invention is an enhancer compound according to the present invention which has an aromatic head group.

In a preferred embodiment, the chemiluminescent composition according to the present invention further comprises a fluorescent agent.

The chemiluminescent composition according to the present invention may further include one or more fluorescent agents, for example, fluorescein sodium, Rhodamine B and/or Rhodamine 6G. The fluorescent agent(s) will emit a kind of fluorescence after receiving light energy from the chemiluminescent signal of the chemiluminogenic compound. It may be that the quantum yield of fluorescein can be far greater than that of the chemiluminogenic compound, so the quantum yield of the chemiluminogenic compound may indirectly improve. For example, fluorescein sodium (9-(o-carboxyphenyl)-6-hydroxy-3H-xanthene-3-ketone disodium) is a water soluble fluorescent agent and has an excitation and emission wavelength of 494 nm and 518 nm, respectively. The quantum yield of fluorescein sodium is up to 0.97. Similarly, Rhodamine series fluorescent agents also have a very high fluorescence quantum yield. The fluorescent agent is preferably used at a concentration of about 0.1 mg/L to about 1 g/L in a chemiluminescent composition according to the present invention.

In a preferred embodiment, the chemiluminescent composition according to the present invention is the chemiluminescent reaction mixture according to a method according to the present invention. Preferably the chemiluminescent composition according to the present invention further comprises nitric acid, hydrogen peroxide and/or sodium hydroxide.

The chemiluminescent composition of the present invention, preferably according to the disclosed embodiments, may be included into a kit by individually packaging the components of the chemiluminescent composition into a multi-package system. In other embodiments according to the present invention, some components may be combined in one container, while the others are stored in separate containers to form a multi-package system. Alternatively, the components may be mixed, and then packaged as a single mixture.

In a $4^{th}$ aspect, the problem underlying the present invention is solved by a kit, preferably for enhancing the chemiluminescence of a chemiluminogenic compound, which comprises at least one chemiluminogenic compound, wherein the chemiluminogenic compound is an acridinium compound, preferably an acridinium ester or an acridinium sulfonamide, more preferably an acridinium ester or an acridinium sulfonamide of formula (II) or formula (III) as disclosed above and one, two or more compounds selected from the group consisting of quarternary amine cationic substances of formula (I) as disclosed above. The problem is preferably solved by a kit for use in the enhancement of the chemiluminescence of a chemiluminogenic compound, wherein the chemiluminogenic compound is an acridinium compound, preferably an acridinium ester or an acridinium sulfonamide, more preferably an acridinium ester or an acridinium sulfonamide of formula (II) or formula (III) as disclosed above and one, two or more compounds selected from the group consisting of quarternary amine cationic substances of formula (I) as disclosed above.

Preferably, the one, two or more compounds selected from the group consisting of quarternary amine cationic substances of formula (I) are enhancers according to the present invention as described above.

In a preferred embodiment, the components of the kit according to the present invention are stored individually or in the form of one, two or more mixtures.

In a preferred embodiment, the at least one chemiluminogenic compound, preferably a compound of formula (II) or formula (III) as disclosed herein, and the one, two or more compounds selected from the group consisting of quarternary amine cationic substances of formula (I) as disclosed herein, are stored together in one mixture in the kit according to the present invention, optionally, further together with sodium hydroxide. Preferably, trigger solution A, preferably comprising nitric acid and hydrogen peroxide, is stored individually in the kit according to the present invention.

In a preferred embodiment, the kit according to the present invention, preferably according to at least one of the disclosed preferred embodiments, comprises a diagnostically useful carrier, preferably a solid carrier, comprising a means for capturing an antigen, antibody or autoantibody in a liquid solution and a means for detecting the antigen, the antibody or the autoantibody bound to the carrier, wherein the means for detecting the antigen, antibody or autoantibody bound to the carrier is labeled with the at least one chemiluminogenic compound, i.e. an acridinium compound, preferably an acridinium ester of formula (II) or an acridinium sulfonamide of formula (III) according to the present invention. According to the present invention it is further preferred that the diagnostically useful carrier is selected from the group comprising a bead, preferably a paramagnetic bead, a test strip, a microtiter plate, a membrane, preferably from the group comprising western blot, line blot and dot blot, a lateral flow device, a glass surface, a slide for microscopy, a microarray and a biochip. In a further preferred embodiment, the diagnostically useful carrier is a line blot, a biochip or a bead, most preferably a bead. Preferably, the diagnostically useful carrier is provided by beads. It is further preferred according to the present invention that the at least one chemiluminogenic compound, wherein the chemiluminogenic compound is an acridinium compound, preferably an acridinium ester or an acridinium sulfonamide, more preferably an acridinium ester or an acridinium sulfonamide of formula (II) or formula (III) according to the present invention, is bound to beads. The binding can be present by non-covalent protein-protein interactions, bridged by protein-protein interactions or can be present by covalent binding.

In a preferred embodiment, the kit according to the present invention further comprises a diagnostically useful carrier as described above, a trigger solution A and a trigger solution B, wherein the trigger solution A includes nitric acid and hydrogen peroxide and the trigger solution B includes sodium hydroxide and the one, two or more compounds selected from the group consisting of quarternary amine cationic substances of formula (I) as defined above and wherein at least trigger solution A and a trigger solution B are stored individually.

In a preferred embodiment, the kit according to the present invention further comprises a means for detecting an antigen, antibody or autoantibody bound to a carrier wherein the means for detecting the antigen, antibody or autoantibody bound to the carrier may be a secondary antibody. Preferably, a secondary antibody is an antibody binding specifically to all antibodies from an antibody class, preferably a mammalian antibody class, more preferably human antibody class such as IgG. Secondary antibodies typically recognize the constant domain of said class but may also recognize other epitopes shared by antibodies from the class of interest, for example a conformational epitope across the 3D structure. A wide range of them is commercially available, for example from Thermo Fisher. It may be a monoclonal or a polyclonal antibody. In a preferred embodiment, the term "recognized", as used herein, means that the secondary antibody binds specifically to the antigen(s), antibody/antibodies or autoantibody/autoantibodies to be detected. A secondary antibody may bind specifically to all isotypes from the antibody class. For example, a secondary antibody to lgG class antibodies may bind to lgG1, lgG2, lgG3 and lgG4 isotypes. This may be achieved by using as a secondary antibody to the class, preferably to IgG class antibodies, a mixture comprising an antibody binding specifically to each IgG isotype or a single antibody which reacts with all isotypes of interest. The use of secondary antibodies is explained in Kruger, N. J., Detection of Polypeptides on Blots Using Secondary Antibodies, in The Protein Protocols Handbook (ed. J. M. Walker), page 967, volume 1996, Springer. Briefly, such secondary antibodies may be generated by immunizing a laboratory animal with the antibody to be recognized or a mixture of the antibodies to be recognized.

In a preferred embodiment, the term "binding specifically", as used herein, preferably means that the binding reaction is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In a preferred embodiment, the chemiluminescent composition, the chemiluminescent reaction mixture and/or the kit according to the present invention, further includes one or more, preferably all reagents from the group comprising stabilizers, preferably a set of stabilizers, washing buffer, antidegradants.

The chemiluminescent composition, the chemiluminescent reaction mixture and/or the kit according to the present invention may further contain a buffer, for maintaining the pH of the reaction system. Appropriate buffers include a carbonate buffer, a diethanolamine buffer, 2-amino-2-methyl-1-propanol, and so on. The buffer may be used at a concentration of about 10 to about 500 mM.

The chemiluminescent composition, the chemiluminescent reaction mixture and/or the kit according to the present invention may further include a preservative, which facilitates the preservation and long-term storage of the reagents. There is no limitation to the type of the preservative, and commercially available preservatives such as Proclin300, sodium azide, Kathon, and Gentamicin may be used. The preservatives may be used at any concentration which will not influence the chemiluminescent reaction.

In a preferred embodiment, the kit according to the present invention further comprises one or more, preferably all reagents from the group comprising calibrators, preferably a set of calibrators, positive controls and negative controls.

According to further different detection uses, the kit according to the present invention may further include corresponding enzyme reagents, labeled enzyme reagent, a solid-phase antibody and/or a manual which instructs the operator.

In a $5^{th}$ aspect, the problem underlying the present invention is solved by a use of the chemiluminescent composition or the chemiluminescent reaction mixture according to the present invention for the manufacture of a kit, a medical device, preferably a diagnostic device, for the diagnosis of a disease. According to the present invention, a medical device is preferably selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

In another aspect, the present invention relates to an immunoassay and/or a method for detecting an analyte of interest in a test sample, the immunoassay and/or the method comprising the steps of:

(a) contacting a test sample suspected of containing an analyte of interest with a first antibody that binds to at least one epitope on the analyte of interest to form a first antibody-analyte complex, wherein the first antibody is immobilized on a solid phase, and further wherein at least one autoantibody in the test sample binds to at least one epitope on the analyte of interest to form an autoantibody-analyte complex, wherein said autoantibody binds to the solid phase;

(b) contacting said mixture comprising a first antibody-analyte complex and an autoantibody-analyte complex, with a second antibody that has been conjugated to a detectable label to form a first antibody-analyte-second antibody complex and an autoantibody-analyte-second antibody complex; wherein the second antibody binds to at least one epitope on the analyte of interest and further wherein, the detectable label is at least one acridinium compound, more preferably an acridinium ester according to formula (II) or an acridinium sulfonamide according to formula (III) as described above according to the present invention;

(c) generating or providing a source of hydrogen peroxide and an enhancer according to formula (I) as described above according to the present invention to the mixture of step (b);

(d) adding a basic solution to the mixture of step (c) to generate a light signal; and (e) measuring the light signal generated by or emitted in step (d) and detecting the analyte of interest in the test sample.

In the above immunoassay or method, the test sample can be whole blood, serum, or plasma.

In a further aspect, the problem underlying the present invention is solved by a chemiluminescent composition of the present invention or a kit of the present invention for use in the diagnosis of a disease.

The present invention is based on the surprising finding of the inventors that by using an enhancer (compound) selected from the group consisting of quarternary amine cationic substances of formula (I) as disclosed herein an enhanced chemiluminescent signal of a chemiluminogenic compound, which is an acridinium compound, preferably an acridinium ester or an acridinium sulfonamide, in a chemiluminescent reaction mixture in a chemiluminescent reaction can be provided.

The inventors have surprisingly found that the addition of an aromatic moiety in a positively charged head group of a quarternary amine cationic substance further enhances the chemiluminescence signal output in comparison to traditional substances, such as cetyltrimethylammonium chloride (CTAC). Furthermore, the inventors have surprisingly found that the length of at least three carbon atoms in the hydrophobic tail of such a quarternary amine cationic substance is of additional importance for the enhancement of the chemiluminescence signal output in comparison to traditional substances, such as cetyltrimethylammonium chloride (CTAC), and in comparison to quarternary amine cationic substances having an aromatic moiety in the positively charged head group but missing a length of at least three carbon atoms in the hydrophobic tail.

Accordingly, the described new method according to the present invention (and related uses, compositions, mixtures and/or substances) allows for even more sensitive quantification of analytes with ultra-low concentration but also favors the signal differentiation in chemiluminescence immunoassays in general.

The chemiluminescent enhancer compounds according to the present invention include simple components with desirable enhancing effects for the chemiluminescence of chemiluminogenic compounds, specifically chemiluminogenic compounds as of formula (II) and/or formula (III) according to the present invention. The chemiluminescent compositions of the present invention provide stable, longlasting and greatly enhanced chemiluminescence signals and may be used in chemiluminescence immunoassays, DNA probe detection, and chemiluminescence analysis of biological membrane protein blotting. The chemiluminescent compositions of the present invention may be widely used in the fields of clinical diagnosis, scientific research, environmental and hygiene detection, and forensic identification. In general, the chemiluminescent enhancer compounds according to the present invention are commercially available and inexpensive. Furthermore, they are suitable for production of chemiluminescent compositions on a large scale.

Unless indicated otherwise, terms used herein have the following meanings:

The term "enhancing" as used herein means that the total light emission of the chemiluminescent reaction and/or the signal to background noise ratio of the chemiluminescent reaction is greater when using the enhancer according to the present invention as in the absence of the enhancer according to the present invention and/or in comparison with so called enhancers which have been used until the present invention (i.e. hexadecyltrimethylammonium chloride; CTAC).

The term "alkyl" as used herein individually or in combination with other groups refers to straight or branched alkyl groups containing 1-20 carbon atoms, such as 1-12, 1-8, and 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$ alkyl" includes $C_{1-4}$ alkyl, $C_{1-3}$ alkyl, methyl, ethyl, n-propyl, isopropyl and tert-butyl. The same rules apply to other groups as used throughout the present specification. Representative examples of alkyl include, but are not limited to, methyl, ethyl, n-propyl, iso-propyl, n-butyl, secbutyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl" as used herein refers to a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one, two, three, four, or five substituents independently selected from the group consisting of alkoxy, alkyl, carboxyl, halo, and hydroxyl.

The term "acyl" as used herein refers to a —$C(O)R_a$ group where $R_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

The term "alkenyl" as used herein refers to a straight or branched chain hydrocarbon containing from 2 to 20 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 20 carbon atoms and containing at least one carbon-carbon triple bond. Representative examples of alkynyl include, but are not limited, to acetylenyl, 1-propynyl, 2-propynyl, 3-butynyl,2-pentynyl, and 1-butynyl.

The term "amido" as used herein refers to an amino group attached to the parent molecular moiety through a carbonyl group (wherein the term "carbonyl group" refers to a —C(O)-group).

The term "amino" as used herein means $—NR_bR_c$, wherein $R_b$ and $R_c$ are independently selected from the group consisting of hydrogen, alkyl and alkylcarbonyl.

The term "aralkyl" as used herein means an aryl group appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

As used herein, the term "carboxy" or "carboxyl" refers to $—CO_2H$ or $—CO_2$.

As used herein, the term "carboxyalkyl" refers to a $—(CH_2)_nCO_2H$ or $—(CH_2)_nCO_2$-group where n is from 1 to 20.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a $—R_dR_e$ group where $R_d$ is an alkylene group and $R_e$ is a cycloalkyl group. A representative example of a cycloalkylalkyl group is cyclohexylmethyl and the like.

The term "halogenide" as used herein includes fluoride, chloride, bromide, and iodide.

As used herein, the term "hydroxyl" means an —OH group.

As used herein, the term "nitro" means a $—NO_2$ group.

As used herein, the term "oxoalkyl" refers to $—(CH_2)_nC(O)R_a$, where $R_a$ is hydrogen, alkyl, cycloalkyl, cycloalkylalkyl, phenyl or phenylalkyl and where n is from 1 to 20.

As used herein, the term "phenylalkyl" means an alkyl group which is substituted by a phenyl group.

As used herein, the term "sulfo" means a $—SO_3H$ or a $—SO_3$ group.

As used herein, the term "sulfoalkyl" refers to a $—(CH_2)_nSO_3H$ or a $—(CH_2)_nSO_3$ group where n is from 1 to 20.

The term "soluble" as used herein refers to the lack of a precipitate.

As used herein, the term "sulfamoyl" refers to $—SO_2—NR_1—$, wherein $R^1$ is selected from the group consisting of hydrogen, alkyl, aryl and alkylcarbonyl.

As used herein, the term "sulfonamide" refers to any amide of a sulfonic acid.

The term "chemiluminescence" as used herein is light generated in a specific reaction of a chemical substance. Singlet molecules are excited and formed as high energy intermediates decompose in a chemical reaction, then the excited singlet molecules return to the ground state, and part of the energy is emitted in the form of luminescence. Therefore, chemiluminescent reactions include two processes: an excitation process and a luminescence process. Some molecular energy will also be dissipated in the excited state because of inter- and intrasystem crossing.

In a preferred embodiment, the term "diagnosis", as used herein, is to be used in its broadest possible sense and may refer to any kind of procedure aiming to obtain information instrumental in the assessment whether a patient, known or an anonymous subject from a cohort, suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient or patients in general with regard to a certain treatment, for example the administration of immunosuppressive drugs, or to find out whether a sample is from such a patient. Such information may be used for a clinical diagnosis, but may also be obtained by an experimental and/or research laboratory for the purpose of general research, for example to determine the proportion of subjects suffering from the disease in a patient cohort or in a population. In other words, the term "diagnosis" comprises not only diagnosing, but also prognosticating and/or monitoring the course of a disease or disorder, including monitoring the response of one or more patients to the administration of a drug or candidate drug, for example to determine its efficacy. While the result may be assigned to a specific patient for clinical diagnostic applications and may be communicated to a medical doctor or institution treating said patient, this is not necessarily the case for other applications, for example in diagnostics for research purposes, where it may be sufficient to assign the results to a sample from an anonymized patient.

In a preferred embodiment, the term "diagnosis" may also refer to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administering to the patient one or more immunosuppressive drugs.

A method according to the present invention is preferably an in vitro method.

According to the present invention, the kit may comprise instructions how to carry out the method according to the present invention.

In a preferred embodiment, any method or use according to the present invention may be intended for a non-diagnostic use, e.g. determining the presence of an autoantibody for a use other than diagnosing a patient. For example, the method or use may be for testing in vitro the efficiency of a medical device designed to remove an autoantibody from a patient's blood, wherein the testing is performed on a liquid other than patient's blood.

In another preferred embodiment, the method may be for confirming the reliability of a diagnostic assay and may involve detecting an antibody to a polypeptide.

In a preferred embodiment, any method or use according to the present invention may be for identifying a subject at risk of suffering from or developing a disease and/or a tumor.

The present invention is further illustrated by the following non-limiting examples from which further features, embodiments, aspects and advantages of the present invention may be taken.

EXAMPLES

Preparation of Acridinium Label and Conjugate Solutions:

1 mg/mL label stock solutions of N-Sulfopropyl-dimethyl-acridinium-N-hydroxysuccinimide (NSP-DMAE-NHS; PerkinElmer Inc., Finnland) and N-Sulfopropyl-acridinium-sulfonamide-N-hydroxysuccinimide (NSP-SA-NHS; BOC Sciences, USA) were each prepared in 100% (v/v) N,N-dimethylformamide (Th. Geyer Hamburg GmbH & Co. Kg, Germany). AffiniPure Goat Anti-Human IgG, Fcy fragment specific (Anti-human IgG-Fcγ; Jackson ImmunoResearch Europe Ltd., UK) was diluted to a final concentration of 0.33 mg/mL in phoshate buffered saline, pH 7.6 and was subsequently incubated with a 10-fold molar excess of NSP-DMAE-NHS or with a 2.5-fold molar excess of NSP-SA-NHS for 2 h at room temperature in an Intelli-Mixer, model RM-2M (Hassa GmbH, Germany) at 10 rpm. The labeling reactions were stopped with addition of 17.4 mM L-lysine (VWR International GmbH, Germany) for 30 min at room temperature during rotation at 10 rpm. Excess of free label was removed from the antibody conjugates during ultrafiltration at 3.800 g in a Heraeus Megafuge 40R centrifuge (Fisher Scientific GmbH, Germany) at 4° C. using a Vivaspin 20, molecular weight cutoff 10 kDa concentrator (VWR International GmbH, Germany) and the buffer was exchanged for phosphate buffered saline, pH 7.4 containing 0.045% (w/v) sodium azide (Merck KgaA, Gemany). The purified antibody conjugates were stored in phosphate buffered saline containing 0.045% (w/v) sodium azide, 1% (w/v) bovine serum albumin (Th. Geyer Hamburg GmbH & Co. Kg, Germany), 0.3% (w/v) Kolliphor® P 188 (Th. Geyer Hamburg GmbH & Co. Kg, Germany) and 0.5 mM Ethylenediaminetetraacetic acid disodium salt (Gerbu Biotechnik GmbH, Germany).

Preparation of Chemiluminescence Trigger Solutions:

Chemiluminescence trigger solution A containing 100 mM nitric acid (VWR International GmbH, Germany) and 0.2% (v/v) hydrogen peroxide (Roth GmbH & Co. KG, Germany) and trigger solution B containing 0.5 M sodium hydroxide (Gerbu Biotechnik GmbH, Germany) were prepared. Trigger solution B was either used lacking any detergent or supplemented with 0.05, 0.1, 0.25 or 0.5% (w/v) of the cationic compounds Hexadecyltrimethylammonium chloride (Merck KgaA, Gemany), Hexadecyltrimethylammonium bromide (Merck KgaA, Gemany) or Tetradecyltrimethylammonium chloride (Merck KgaA, Gemany) all of which lack an aromatic head group. Alternatively, trigger solution B was supplemented with 0.05, 0.1, 0.25 or 0.5% (w/v) of the cationic compounds Hexadecylbenzyldimethylammonium chloride (Merck KgaA, Gemany; CAS 122-18-9), Benzalkonium chloride (Merck KgaA, Gemany; CAS 63449-41-2), Alkyl ($C_{12}$-$C_{14}$) dimethylethylbenzyl-ammonium chloride (Alfa Chemistry, USA; CAS 85409-23-0) or Benzyldimethyldodecylammonium chloride (VWR International GmbH, Germany; CAS 139-07-1), all of which contain an aromatic head group or with Benzyltriethylammonium chloride (Merck KgaA, Gemany) which contains an aromatic head group but lacks a prolonged hydrophobic tail of at least three carbon atoms.

Measurement of Chemiluminescence Signal Intensities:

NSP-DMAE-NHS and NSP-SA-NHS label stock solutions were diluted to a final concentration of 1 nM and antibody conjugates were diluted to a final concentration of 0.1 μg/mL in phoshate buffered saline, pH 7.4. 10 μL each of these dilutions were transferred to a well of a 96-well LumiNunc™ plate (VWR International GmbH, Germany) and chemiluminescence signal intensities were measured on a LB 960 Centro Microplate Luminometer (Berthold Technologies Gmbh & Co. KG, Germany) in the presence of 100 μL each of chemiluminescence trigger A and of different trigger B solutions, the latter varying in the identity and concentration of the cationic compound. After injection of trigger A with middle speed, the mixtures were incubated for 1 sec during mixing in double orbit mode with normal speed. Chemiluminescence intensities in relative light units (RLU) were recorded every 50 ms over a total time of 1.5 sec upon addition of the various trigger B solutions with low injection speed. All of the samples were measured in four technical replicates. In control experiments all different trigger B solutions were injected in combination with trigger A into empty wells of the 96-well plate. The latter experiments reflect the signal background generated by the different trigger solutions.

Data Analysis:

For graphic presentation of the observed chemiluminescence kinetics a representative data set was chosen from the four technical replicates and the signal intensities in RLU were plotted against time. Additionally, total signal intensities were calculated by addition of all RLU values observed in the 1.5 sec time frame. The background signal intensities of the different trigger B solutions were subtracted from the total signal intensities and all background-corrected total signal intensities were set in comparison.

Example 1

Three representative enhancer compounds (compounds 1-3) according to the present invention were chosen for the analysis. These molecules are all based on a cationic, quarternary ammonium compound containing an aromatic moiety adjacent to the quarternary ammonium. The enhancer compounds according to the present invention were tested against a common enhancer substance CTAC (as for example proposed in U.S. Pat. No. 4,927,769). In contrast, CTAC does not contain an aromatic moiety adjacent to the quarternary ammonium.

Figure 2:
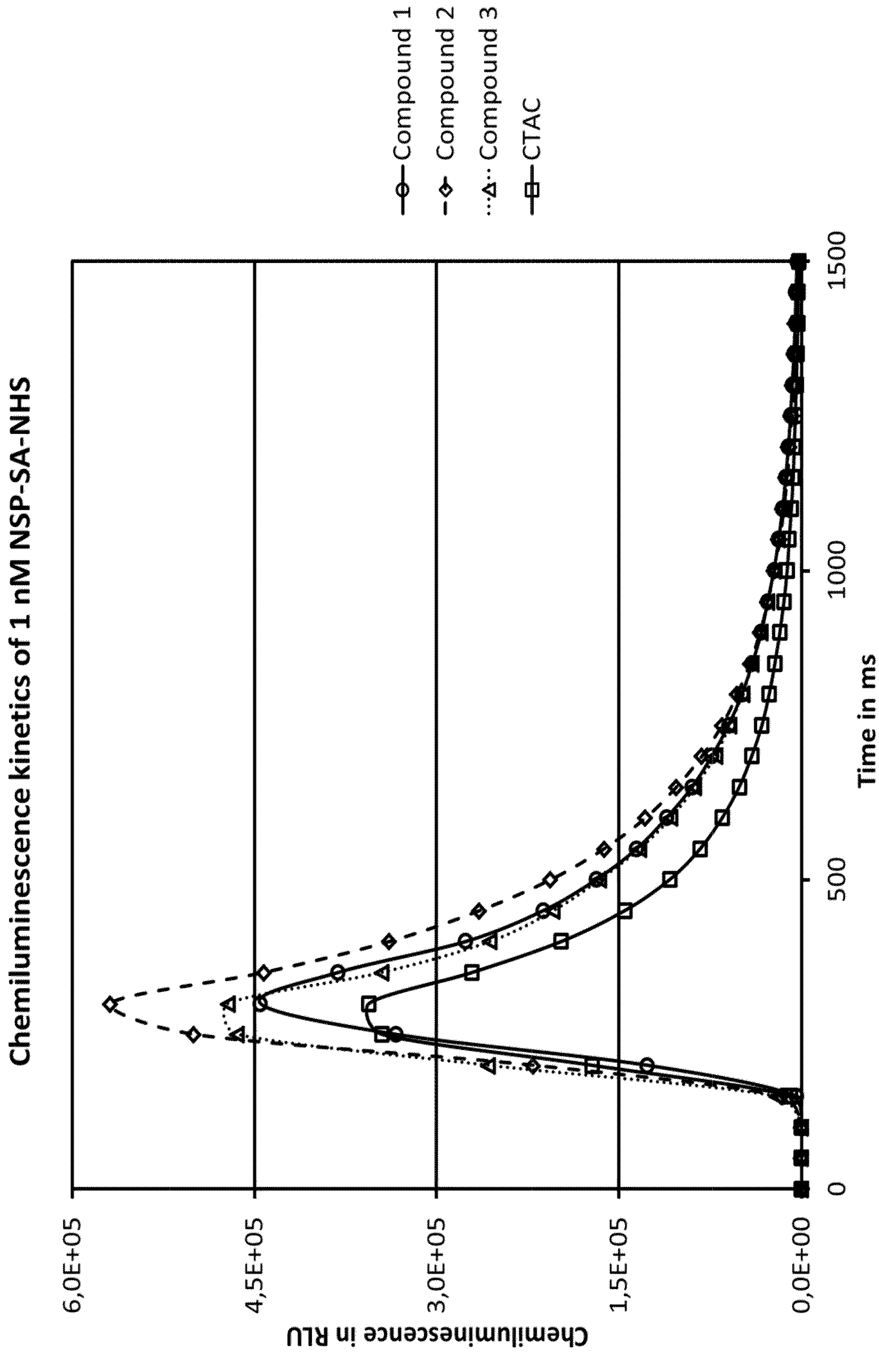
FIG. 2 shows the chemiluminescence kinetics of 1 nM NSP-SA-NHS in the presence of 0.5% (w/v) of three different cationic compounds, each with an aromatic head group (compound 1: Benzyldimethylhexadecylammonium chloride; compound 2: Benzalkonium chloride; compound 3: Alkyl ($C_{12}$-$C_{14}$) dimethylethylbenzyl-ammonium chloride) or in the presence of 0.5% (w/v) of the cationic detergent CTA C lacking an aromatic head group.
Figure 3:
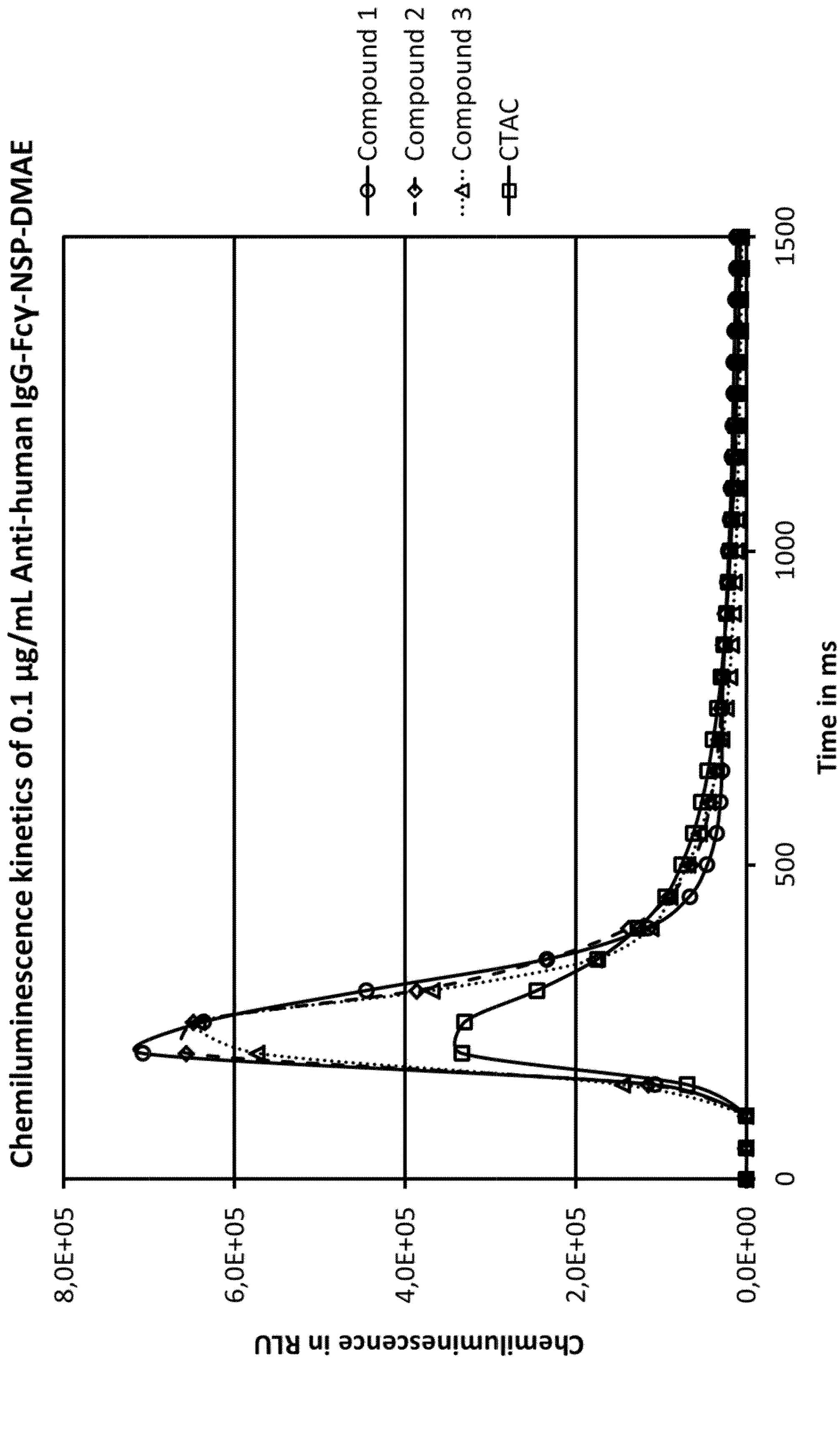
FIG. 3 shows the chemiluminescence kinetics of 0.1 μg/mL Anti-human IgG-Fcγ-NSP-DMAE in the presence of 0.5% (w/v) of three different cationic compounds, each with an aromatic head group (compound 1: Benzyldimethylhexadecylammonium chloride; compound 2: Benzalkonium chloride; compound 3: Alkyl ($C_{12}$-$C_{14}$) dimethylethylbenzyl-ammonium chloride) or in the presence of 0.5% (w/v) of the cationic detergent CTA C lacking an aromatic head group.
Figure 4:
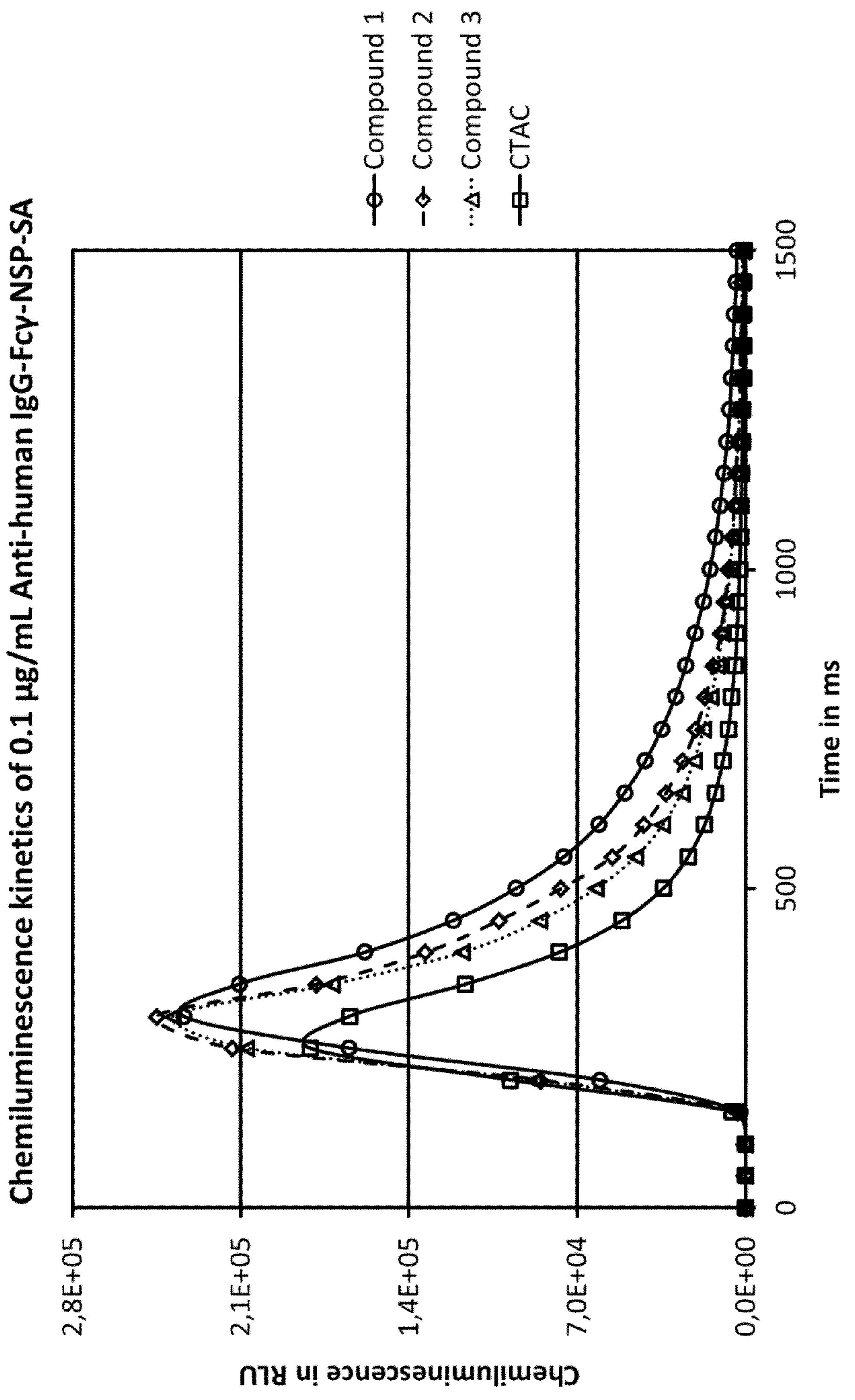
FIG. 4 shows chemiluminescence kinetics of 0.1 μg/mL Anti-human IgG-Fcγ-NSP-SA in the presence of 0.5% (w/v) of three different cationic compounds, each with an aromatic head group (compound 1: Benzyldimethylhexadecylammonium chloride; compound 2: Benzalkonium chloride; compound 3: Alkyl ($C_{12}$-$C_{14}$) dimethylethylbenzyl-ammonium chloride) or in the presence of 0.5% (w/v) of the cationic detergent CTA C lacking an aromatic head group.
Figure 5:
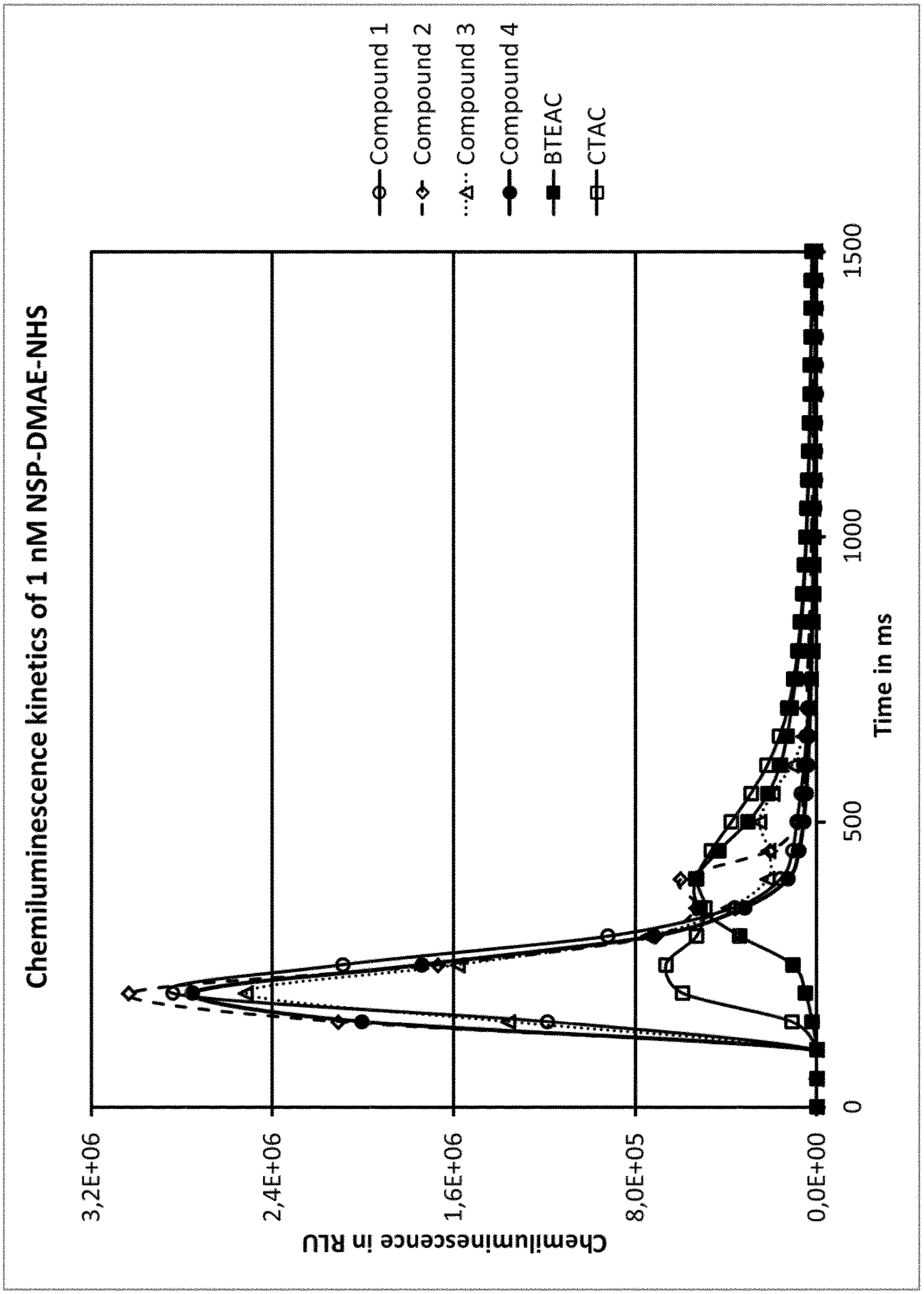
FIG. 5 shows the chemiluminescence kinetics of 1 nM NSP-DMAE-NHS in the presence of 0.5% (w/v) of four different cationic compounds, each with an aromatic head group and a prolonged hydrophobic tail with at least three carbon atoms (compound 1: Benzyldimethylhexadecylammonium chloride; compound 2: Benzalkonium chloride; compound 3: Alkyl ($C_{12}$-$C_{14}$) dimethylethylbenzyl-ammonium chloride; compound 4: Benzyldimethyldodecylammonium chloride) or in the presence of 0.5% (w/v) Benzyltriethylammonium chloride (BTEA C) containing an aromatic head group but lacking a prolonged hydrophobic tail or in the presence of 0.5% (w/v) CTAC lacking an aromatic head group but containing a prolonged hydrophobic tail.
Figure 6:
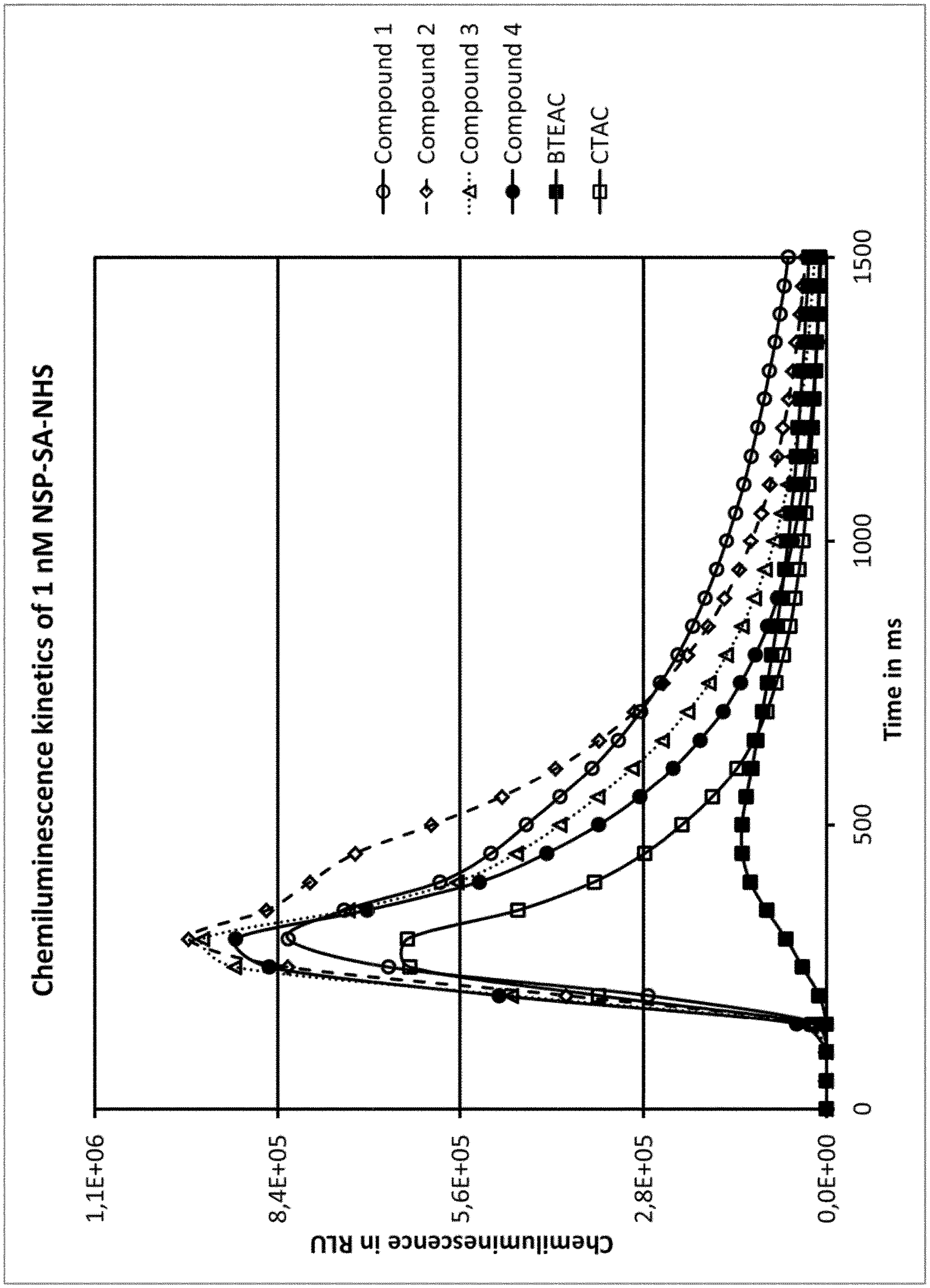
FIG. 6 shows the chemiluminescence kinetics of 1 nM NSP-SA-NHS in the presence of 0.5% (w/v) of four different cationic compounds, each with an aromatic head group and a prolonged hydrophobic tail with at least three carbon atoms (compound 1; Benzyldimethylhexadecylammonium chloride; compound 2: Benzalkonium chloride; compound 3: Alkyl ($C_{12}$-$C_{14}$) dimethylethylbenzyl-ammonium chloride; compound 4: Benzyldimethyldodecylammonium chloride) or in the presence of 0.5% (w/v) BTEA C containing an aromatic head group but lacking a prolonged hydrophobic tail or in the presence of 0.5% (w/v) CTAC lacking an aromatic head group but containing a prolonged hydrophobic tail.
Figure 7:
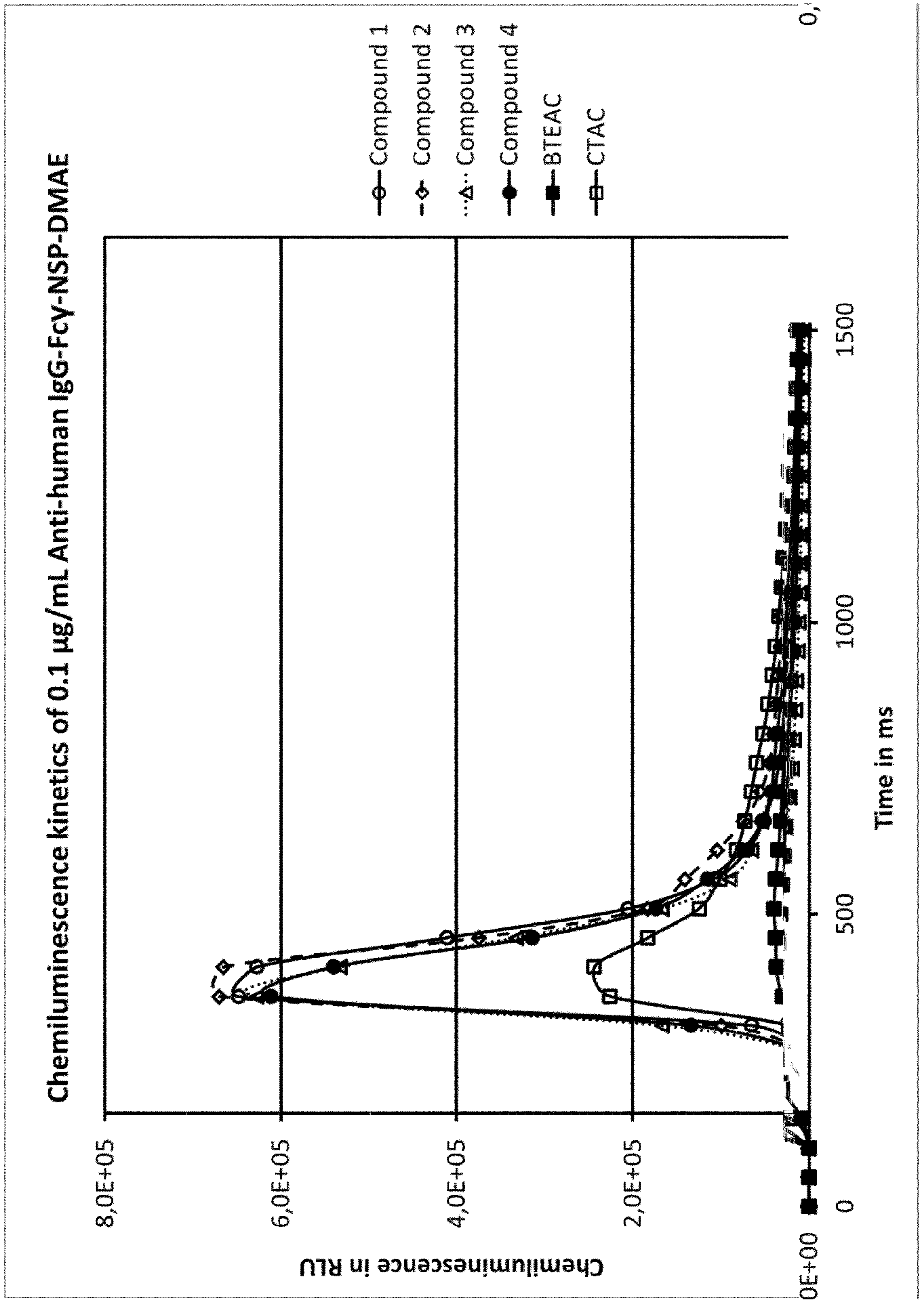
FIG. 7 shows the chemiluminescence kinetics of 0.1 μg/mL Anti-human IgG-Fcγ-NSP-DMAE in the presence of 0.5% (w/v) of four different cationic compounds, each with an aromatic head group and a prolonged hydrophobic tail with at least three carbon atoms (compound 1: Benzyldimethylhexadecylammonium chloride; compound 2: Benzalkonium chloride; compound 3: Alkyl ($C_{12}$-$C_{14}$) dimethylethylbenzyl-ammonium chloride; compound 4: Benzyldimethyldodecylammonium chloride) or in the presence of 0.5% (w/v) BTEAC containing an aromatic head group but lacking a prolonged hydrophobic tail or in the presence of 0.5% (w/v) CTAC lacking an aromatic head group but containing a prolonged hydrophobic tail.
Figure 8:
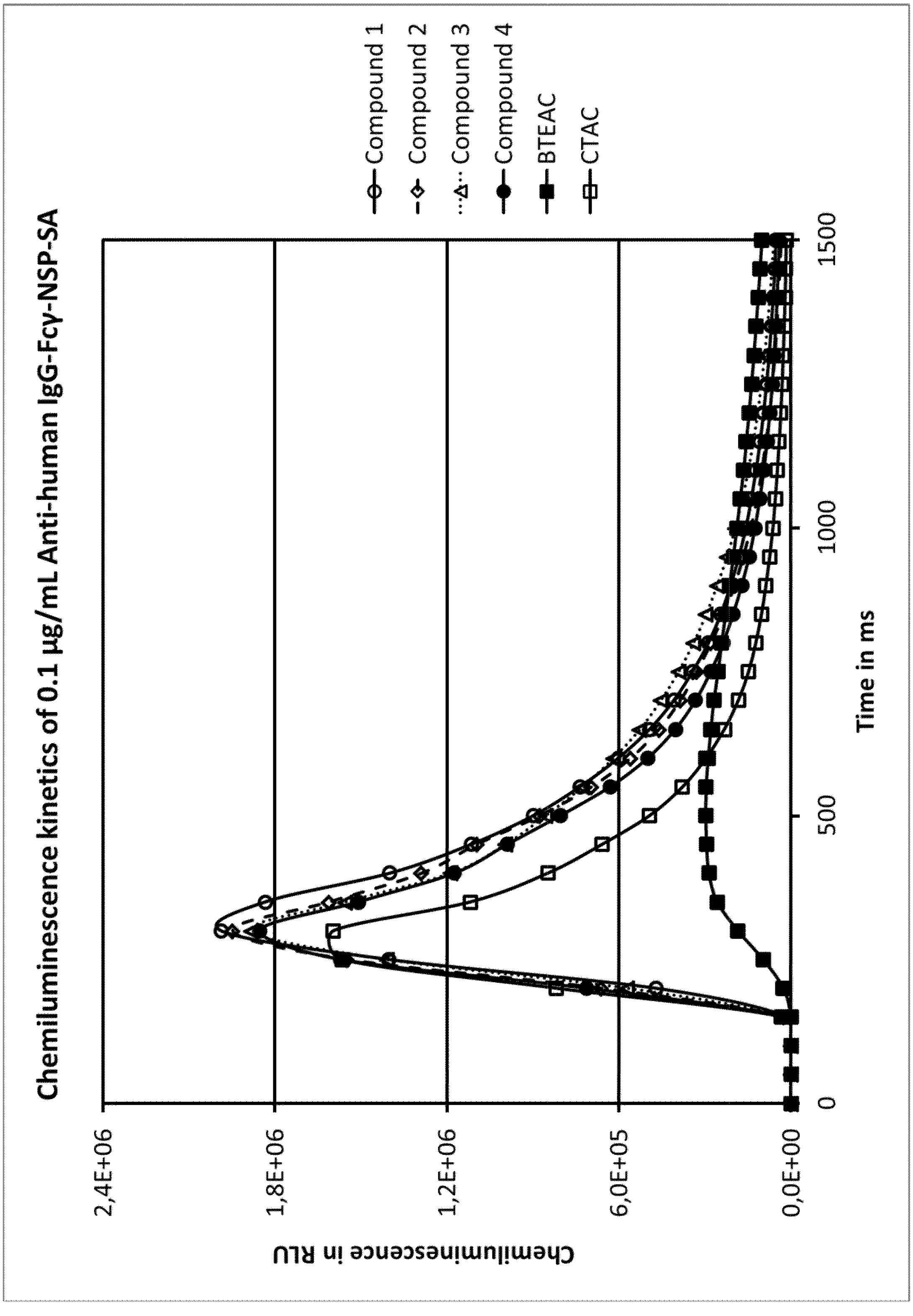
FIG. 8 shows chemiluminescence kinetics of 0.1 μg/mL Anti-human IgG-Fcγ-NSP-SA in the presence of 0.5% (w/v) of four different cationic compounds, each with an aromatic head group and a prolonged hydrophobic tail with at least three carbon atoms (compound 1: Benzyldimethylhexadecylammonium chloride; compound 2: Benzalkonium chloride; compound 3: Alkyl ($C_{12}$-$C_{14}$) dimethylethylbenzyl-ammonium chloride; compound 4: Benzyldimethyldodecylammonium chloride) or in the presence of 0.5% (w/v) BTEA C containing an aromatic head group but lacking a prolonged hydrophobic tail or in the presence of 0.5% (w/v) CTAC lacking an aromatic head group but containing a prolonged hydrophobic tail.

Four representative analytes were chosen to investigate the effect of the enhancer compounds according to the present invention in comparison to the common enhancer substance already known in the prior art on the chemiluminescence signal generated by these analytes (FIG. 1-4). The chosen analytes include the acridinium compounds NSP-DMAE-NHS and NSP-SA-NHS in free- (FIG. 1-2) and in antibody-bound-form (FIG. 3-4). A polyclonal Anti-human IgG-Fcγantibody from goat was chosen for conjugation with both types of acridinium label.

Acridinium label, conjugate solutions and chemiluminescence trigger solutions were obtained according to the methods disclosed above. Measurement of chemiluminescence signal intensities was performed and data was analysed as described above.

Results:

A 43% increase in signal output using Benzyldimethylhexadecylammonium chloride (compound 1) with analyte NSP-DMAE-NHS (FIG. 1, Table 3) was observed in comparison with the enhancer substance CTAC for the same analyte.

Benzalkonium chloride (compound 2) and Alkyl ($C_{12}$-$C_{14}$) dimethylethylbenzyl-ammonium chloride (compound 3) also resulted in a 19% and 15% signal increase in comparison with CTAC with NSP-DMAE-NHS as analyte, respectively.

A similar result was obtained when the analyte was switched to NSP-SA-NHS (FIG. 2, Table 3).

Compound 1 (Benzyldimethylhexadecylammonium chloride) led to a signal increased by 67% compared to the substance CTAC. Moreover, a 58% and 40% signal increase with compounds 2 and 3 were observed for this analyte in comparison to CTAC, respectively.

Additionally, it was found that the enhancement of the signal output observed for both examples of acridinium-based probes in the free form could also be observed when the probes were covalently attached to an antibody, the latter typically required for immunoassays.

In this scenario, compound 1 (Benzyldimethylhexadecylammonium chloride) led to a 45% and a 66% signal increase for the analytes Anti-human IgG-Fcγ-NSP-DMAE (FIG. 3, Table 3) and Anti-human IgG-Fcγ-NSP-SA (FIG. 4, Table 3), respectively in comparison with signal generation for those analytes in the presence of CTAC. Compound 2 (Benzalkonium chloride) also increased the signal of these two antibody conjugates by 40% and by 52%, respectively. Moreover, a 25% and a 35% signal increase in the presence of compound 3 (Alkyl ($C_{12}$-$C_{14}$) dimethylethylbenzylammonium chloride) for the two analytes were observed in comparison with the signal generation in the presence of CTAC.

Example 2

Description:

In order to test the effect of the chain length within the hydrophobic tail of the substances on chemiluminescence enhancement further experiments were performed with compounds 1-3 (as described in Example 1), with the common enhancer CTAC, with an additional cationic enhancer according to the present invention (compound 4; Benzyldimethyldodecylammonium chloride) and with the additional substance BTEAC (Benzyltriethylammoniumchloride), which contains a chain length of less than three carbon atoms in the hydrophobic tail (FIGS. 5-8). These additional experiments were performed as described above and as described in Example 1, respectively.

Results:

Similarly to the compounds 1-3, compound 4 enhanced the chemiluminescence of 1 nM NSP-DMAE-NHS (FIG. 5), of 1 nM NSP-SA-NHS (FIG. 6), of 0.1 μg/mL Anti-human IgG-Fcγ-NSP-DMAE (FIG. 7) and of 0.1 μg/mL Anti-human IgG-Fcγ-NSP-SA (FIG. 8) compared with the common enhancer CTAC. In this experiment, compounds 1-3 increased the chemiluminescence of 1 nM NSP-DMAE-NHS by 45-79%, of 1 nM NSP-SA-NHS by 62-102%, of 0.1 μg/mL Anti-human IgG-Fcγ-NSP-DMAE by 46-63% and of 0.1 μg/mL Anti-human IgG-Fcγ-NSP-SA by 47-50% compared with the common enhancer CTAC (Tab. 4). Similarly, compound 4 increased the chemiluminescence of 1 nM NSP-DMAE-NHS by 50%, of 1 nM NSP-SA-NHS by 47%, of 0.1 μg/mL Anti-human IgG-Fcγ-NSP-DMAE by 50% and of 0.1 μg/mL Anti-human IgG-Fcγ-NSP-SA by 40% compared with the common enhancer CTAC (Tab. 4).

For BTEAC, a reduced chemiluminescence was observed with all four analytes compared with the common enhancer CTAC (FIGS. 5-8 and Tab. 4). Although this substance contains an aromatic head group, this substance does not function as an equivalent chemiluminescence enhancer, most likely and not being bound to any theory, because the chain length of the hydrophobic tail is too short to form micellular structures.

TABLE 3

Comparison of background-corrected total signal intensities of four different analytes in the presence of 0.5% (w/v) of three different cationic enhancer compounds, each having an aromatic head group (compounds 1-3) or in the presence of 0.5% (w/v) of the cationic detergent CTAC lacking an aromatic head group.

| | Analyte | | | |
|---|---|---|---|---|
| Compound | NSP-DMAE-NHS | NSP-SA-NHS | Anti-human IgG-Fcγ-NSP-DMAE | Anti-human IgG-Fcγ-NSP-SA |
| Benzyldimethylhexadecylammonium chloride (compound 1) | 4712949 RLU (+43%) | 3631369 RLU (+67%) | 2707416 RLU (+45%) | 1449182 RLU (+66%) |
| Benzalkonium chloride (compound 2) | 3913778 RLU (+19%) | 3432574 RLU (+58%) | 2621080 RLU (+40%) | 1325083 RLU (+52%) |
| Alkyl($C_{12}$-$C_{14}$)dimethylethylbenzylammonium chloride (compound 3) | 3809207 RLU (+15%) | 3042201 RLU (+40%) | 2339403 RLU (+25%) | 1175726 RLU (+35%) |
| CTAC | 3299926 RLU | 2169527 RLU | 1871550 RLU | 872358 RLU |

TABLE 4

Comparison of background-corrected total signal intensities of four different analytes in the presence of 0.5% (w/v) of four different cationic enhancer compounds, each having an aromatic head group and a prolonged hydrophobic tail with at least three carbon atoms (compounds 1-4) or in the presence of 0.5% (w/v) Benzyltriethylammonium chloride (BTEAC) containing an aromatic head group but lacking a prolonged hydrophobic tail or in the presence of 0.5% (w/v) of the cationic detergent CTAC lacking an aromatic head group but containing a prolonged hydrophobic tail.

| | Analyte | | | |
|---|---|---|---|---|
| Compound | NSP-DMAE-NHS | NSP-SA-NHS | Anti-human IgG-Fcγ-NSP-DMAE | Anti-human IgG-Fcγ-NSP-SA |
| Benzyldimethylhexadecyl-ammonium chloride (compound 1) | 9285851 RLU (+74%) | 7687351 RLU (+86%) | 2545936 RLU (+55%) | 13400308 RLU (+48%) |
| Benzalkonium chloride (compound 2) | 9554986 RLU (+79%) | 8351873 RLU (+102%) | 2667518 RLU (+63%) | 13568679 RLU (+50%) |
| Alkyl($C_{12}$-$C_{14}$)dimethylethyl-benzylammonium chloride (compound 3) | 7746405 RLU (+45%) | 6669609 RLU (+62%) | 2389234 RLU (+46%) | 13333146 RLU (+47%) |
| Benzyldimethyldodecyl-ammonium chloride (compound 4) | 8015307 RLU (+50%) | 6074325 RLU (+47%) | 2450210 RLU (+50%) | 12677099 RLU (+40%) |
| BTEAC | 3663184 RLU (−31%) | 1939935 RLU (−53%) | 676605 RLU (−59%) | 5143731 RLU (−43%) |
| CTAC | 5333619 RLU | 4125130 RLU | 1637564 RLU | 9041121 RLU |

Together, the data obtained in the described examples show that all four tested compounds which represent examples of enhancers presented by the present invention were able to increase the signal generated by all tested acridinium-based analytes in comparison to the signal generation by the same acridinium-based analytes in the presence of a common enhancer, as CTAC.

Moreover, these new chemiluminescence enhancers all share a molecular structure containing a cationic, quarternary ammonium compound linked to an aromatic moiety, i.e. aromatic head group, and a minimum chain length of at least three carbon atoms in the hydrophobic tail of the enhancer. It is likely that all substances which contain these molecular moieties, i.e. the aromatic head group and the minimum chain length of at least three carbon atoms in the hydrophobic tail, would similarly enhance the chemiluminescence generated by acridinium-based analytes in comparison to enhancer substances lacking these molecular moieties, i.e. the aromatic head group and the minimum chain length of at least three carbon atoms in the hydrophobic tail. Substances with a shorter chain length in the hydrophobic tail do not similarly enhance the chemiluminescence, most likely because they do not form micellular structures, which are supposed to favor the chemiluminescence enhancement. While not being bound by theory, it is further believed that the newly presented cationic chemiluminescence enhancers according to the present invention favors the chemiluminescence reaction process by direct interaction with the acridinium ring forming so-called hydrophobic TT-TT stacking interactions. In this fashion, the acridinium label may be efficiently recruited and positioned for reaction with the hydrogen peroxide anion, the latter attracted by the positive charge of the adjacent cationic ammonium ion.

The data, figures, instruments, reagents and steps herein should be understood to be illustrative, but not restrictive. Although the present disclosure was described with reference to the above concrete embodiments, many modifications and variances will be apparent to skilled persons in the art. All the modifications and variances also fall within the spirit and scope of the disclosure.

The invention claimed is:

1. A method for enhancing a chemiluminescent signal of a chemiluminogenic compound in a chemiluminescent reaction mixture in a chemiluminescent reaction, the method comprising:

oxidizing the chemiluminogenic compound in the presence of an effective amount of an enhancer to obtain an enhanced chemiluminescent signal, wherein the chemiluminogenic compound is an acridinium compound, wherein said enhancer is a compound or a mixture of two, three, or more compounds, and wherein said enhancer compound or each of the enhancer compounds is at least one selected from the group consisting of quaternary amine cationic substances of formula (I)

formula (I)

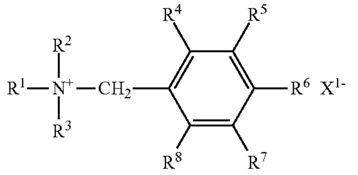

wherein $R^1$ is $C_3$-$C_{20}$ alkyl or alkenyl; and $R^2$ and $R^3$ are independently from each other $C_1$-$C_4$ alkyl or alkenyl; and $R^4$, $R^5$, $R^6$, $R^7$ and $R^8$ are independently from each other hydrogen, alkyl, or alkenyl; and $X^{1-}$ is halogenide or a hydroxyl-ion.

2. The method according to claim 1, wherein the enhancer compound is a quaternary amine cationic substance of formula (I), and wherein $R^1$ is $C_5$-$C_{18}$ alkyl or alkenyl;

$R^2$ and $R^3$ are independently from each other methyl, ethyl, propyl, or butyl preferably methyl;

$R^4$, $R^5$, $R^6$, $R^7$ and $R^8$ are independently from each other hydrogen, alkyl, or alkenyl; and/or $X^{1-}$ is chloride or bromide.

3. The method according to claim 1, wherein said enhancer, at least one compound of said enhancer, or each compound of said enhancer is at least one selected from the group consisting of Benzyldimethylicosylammonium chloride,
Benzyldimethylnonadecylammonium chloride,
Benzyldimethyloctadecylammonium chloride,
Benzyldimethylheptadecylammonium chloride,
Benzyldimethylhexadecylammonium chloride,
Benzyldimethylpentadecylammonium chloride,
Benzyldimethyltetradecylammonium chloride,
Benzyldimethyltridecylammonium chloride,
Benzyldimethyldodecylammonium chloride,
Benzyldimethylundecylammonium chloride,
Benzyldimethyldecylammonium chloride,
Benzyldimethylnonylammonium chloride,
Benzyldimethyloctylammonium chloride,
Benzalkonium chloride,
Benzyldimethylheptylammonium chloride,
Benzyldimethylhexylammonium chloride,
Benzyldimethylpentylammonium chloride,
Benzyldimethylbutylammonium chloride,
Benzyldimethylpropylammonium chloride,
Benzyltripropylammonium chloride,
Benzyldipropylethylammonium chloride,
Benzyldiethylpropylammonium chloride,
Benzyldipropylmethylammonium chloride,
Benzylpropylethylmethylammonium chloride,
Benzyltributylammonium chloride,
Benzyldibutylpropylammonium chloride,
Benzyldipropylbutylammonium chloride,
Benzylbutylpropylethylammonium chloride,
Benzylbutylpropylmethylammonium chloride,
Benzylbutylethylmethylammonium chloride,
Benzyldiethylbutylammonium chloride,
$C_{12-14}$-alkyldimethyl (ethylbenzyl) ammonium chloride,
Dodecyl (ethylbenzyl) dimethylammonium chloride,
Tetradecyldimethyl (ethylbenzyl) ammonium chloride,
Octadecyldimethyl (ar-ethylbenzyl) ammonium chloride, and the respective aforementioned compounds containing bromide instead of chloride.

4. The method according to claim 1, wherein the effective amount of said enhancer in the chemiluminescent reaction mixture is 0.001% by weight per volume (w/v) or greater, based on a total volume of the chemiluminescent reaction mixture.

5. The method according to claim 1, wherein the enhancer is combined with the chemiluminogenic compound in the chemiluminescent reaction mixture before, simultaneously to, or shortly after the start of the chemiluminescent reaction.

6. The method according to claim 1, wherein the chemiluminescent signal generated by the chemiluminescent reaction is detected for a fixed duration of time, and wherein a duration of the detection starts with the start of the chemiluminescent reaction.

7. The method according to claim 1, wherein the chemiluminescent reaction mixture additionally includes hydrogen peroxide, nitric acid, and/or sodium hydroxide.

8. The method according to claim 1, wherein the chemiluminogenic compound is an acridinium ester according to formula (II)

formula (II)

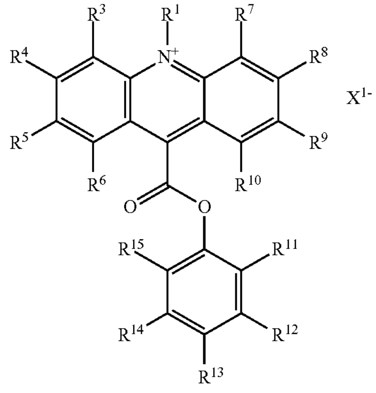

wherein $R^1$ is an alkyl, alkenyl, alkynyl, aryl or aralkyl, sulfoalkyl, carboxyalkyl, or oxoalkyl; and wherein $R^3$ through $R^{15}$ are each independently from each other at least one selected from the group consisting of hydrogen, alkyl, alkenyl, alkynyl, aryl or aralkyl, amino, amido, acyl, alkoxyl, hydroxyl, carboxyl, halogen, halogenide, nitro, cyano, sulfo, sulfoalkyl, sulfamoyl, carboxyalkyl, succinimidyl ester, oxoalkyl, and any other leaving group; and optionally, if present, $X^{1-}$ is an anion;

or an acridinium sulfonamide according to formula (III)

formula (III)

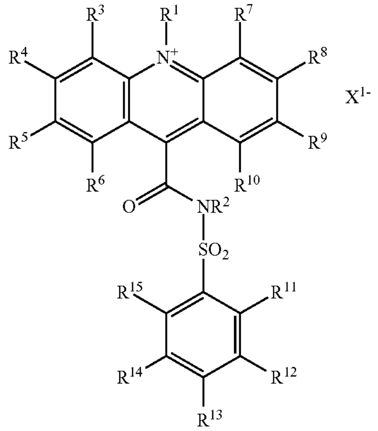

wherein $R^1$ is selected from the group consisting of alkyl, alkenyl, alkynyl, aryl, aralkyl, sulfoalkyl, carboxyalkyl, and oxoalkyl, and wherein $R^2$ through $R^{15}$ are each independently from each other at least one selected from the group consisting of hydrogen, alkyl, alkenyl, alkynyl, aryl or aralkyl, amino, amido, acyl, alkoxyl, hydroxyl, carboxyl, halogen, halogenide, nitro, cyano, sulfo, sulfoalkyl, sulfamoyl, carboxyalkyl, succinimidyl, oxoalkyl, and any other leaving group; and optionally, if present, $X^{1-}$ is an anion.

9. The method according to claim 1, wherein the acridinium compound is acridinium ester or an acridinium sulfonamide.

10. The method according to claim 1, wherein $X^{1-}$ is chloride or bromide.

11. The method according to claim 1, wherein the effective amount of said enhancer in the chemiluminescent reaction mixture is 0.2% by w/v or greater, based on a total volume of the chemiluminescent reaction mixture.

12. The method according to claim 1, wherein the enhancer is combined with the chemiluminogenic compound in the chemiluminescent reaction mixture simultaneously to the start of the chemiluminescent reaction.

13. The method according to claim 1, wherein the chemiluminescent signal generated by the chemiluminescent reaction is detected for a fixed duration of time, and wherein the duration of time is from 0.5 to 10 seconds and wherein a duration of the detection starts with the start of the chemiluminescent reaction.

14. A chemiluminescent composition, comprising:

at least one compound selected from the group consisting of quaternary amine cationic substances of formula (I)

formula (I)

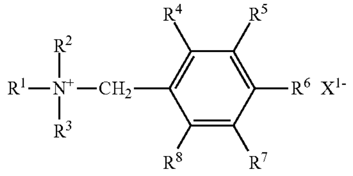

wherein $R^1$ is $C_3$-$C_{20}$ alkyl or alkenyl; and $R^2$ and $R^3$ are independently from each other $C_1$-$C_4$ alkyl or alkenyl; and $R^4$, $R^5$, $R^6$, $R^7$ and $R^8$ are independently from each other hydrogen, alkyl, or alkenyl; and $X^{1-}$ is halogenide or hydroxyl-ion, and at least one chemiluminogenic compound, wherein the chemiluminogenic compound is an acridinium compound.

15. The chemiluminescent composition according to claim 13, for use in the diagnosis of a disease.

16. A kit, comprising:

at least one chemiluminogenic compound, wherein the chemiluminogenic compound is an acridinium compound, and one, two, or more compounds selected from the group consisting of quaternary amine cationic substances of formula (I)

formula (I)

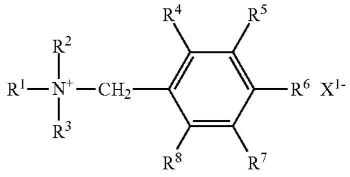

wherein $R^1$ is $C_3$-$C_{20}$ alkyl or alkenyl; and $R^2$ and $R^3$ are independently from each other $C_1$-$C_4$ alkyl or alkenyl; and $R^4$, $R^3$, $R^6$, $R^7$ and $R^8$ are independently from each other hydrogen, alkyl, or alkenyl; and $X^{1-}$ is halogenide or hydroxyl-ion.

17. The kit according to claim 16, further comprising;

a diagnostically useful carrier, comprising a capturer for an antigen, antibody or autoantibody in a liquid solution and a detector for the antigen, the antibody or the autoantibody bound to the carrier, wherein the detector for the antigen, antibody or autoantibody bound to the carrier is labeled with the at least one chemiluminogenic compound.

18. The kit according to claim 16, for use in diagnosis of a disease.

* * * * *